US011471564B2

(12) United States Patent
Nakamura et al.

(10) Patent No.: US 11,471,564 B2
(45) Date of Patent: Oct. 18, 2022

(54) ANGIOGENIC AGENT AND METHOD OF MANUFACTURING THE SAME

(71) Applicant: FUJIFILM Corporation, Tokyo (JP)

(72) Inventors: Kentaro Nakamura, Ashigarakami-gun (JP); Ryo Kogawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/804,823

(22) Filed: Feb. 28, 2020

(65) Prior Publication Data

US 2020/0268943 A1 Aug. 27, 2020

Related U.S. Application Data

(63) Continuation of application No. PCT/JP2018/032162, filed on Aug. 30, 2018.

(30) Foreign Application Priority Data

Aug. 30, 2017 (JP) .............................. JP2017-165416
Feb. 26, 2018 (JP) .............................. JP2018-032351

(51) Int. Cl.
| | | |
|---|---|---|
| A61L 27/38 | (2006.01) | |
| A61K 35/28 | (2015.01) | |
| A61L 27/18 | (2006.01) | |
| A61L 27/26 | (2006.01) | |
| A61L 27/44 | (2006.01) | |
| A61L 27/56 | (2006.01) | |

(52) U.S. Cl.
CPC .......... *A61L 27/3834* (2013.01); *A61K 35/28* (2013.01); *A61L 27/18* (2013.01); *A61L 27/26* (2013.01); *A61L 27/44* (2013.01); *A61L 27/56* (2013.01)

(58) Field of Classification Search
None
See application file for complete search history.

(56) References Cited

U.S. PATENT DOCUMENTS

| | | |
|---|---|---|
| 5,314,471 A | 5/1994 | Brauker et al. |
| 5,545,223 A | 8/1996 | Neuenfeldt et al. |
| 5,593,440 A | 1/1997 | Brauker et al. |
| 5,741,330 A | 4/1998 | Brauker et al. |
| 5,800,829 A * | 9/1998 | Dionne ................ A61K 9/0024 424/490 |
| 5,938,929 A | 8/1999 | Shimagaki et al. |
| 2003/0124722 A1 | 7/2003 | Ohgawara et al. |
| 2007/0237749 A1* | 10/2007 | Wang ........................ A01N 1/02 424/93.7 |
| 2010/0124564 A1 | 5/2010 | Martinson et al. |
| 2010/0196329 A1 | 8/2010 | Ra et al. |
| 2010/0196433 A1 | 8/2010 | Williams et al. |
| 2012/0115224 A1 | 5/2012 | Ochiai et al. |
| 2012/0329157 A1 | 12/2012 | Nakamura |
| 2013/0071441 A1 | 3/2013 | Iwazawa et al. |
| 2014/0107574 A1 | 4/2014 | Pogge Von Strandmann |
| 2015/0202344 A1 | 7/2015 | Iwazawa et al. |
| 2015/0246072 A1 | 9/2015 | Bhatia et al. |
| 2015/0352252 A1 | 12/2015 | Nakamura et al. |
| 2016/0310541 A1 | 10/2016 | Bou Aoun et al. |
| 2017/0035943 A1 | 2/2017 | Simon et al. |
| 2017/0266626 A1 | 9/2017 | Kayama et al. |
| 2019/0262122 A1 | 8/2019 | Mochizuki et al. |
| 2019/0262509 A1 | 8/2019 | Mochizuki et al. |

FOREIGN PATENT DOCUMENTS

| | | |
|---|---|---|
| CN | 1158273 A | 9/1997 |
| CN | 1730099 A | 2/2006 |
| CN | 1927413 A | 3/2007 |
| CN | 101224392 A | 7/2008 |
| CN | 101466360 A | 6/2009 |
| CN | 101558151 A | 10/2009 |
| CN | 201337642 Y | 11/2009 |
| CN | 102282254 A | 12/2011 |
| CN | 103480278 A | 1/2014 |
| CN | 104768586 A | 7/2015 |
| CN | 105025940 A | 11/2015 |
| CN | 106573203 A | 4/2017 |
| EP | 0550798 A1 | 7/1993 |
| EP | 2578246 A2 | 4/2013 |
| EP | 2962703 A1 | 1/2016 |
| EP | 3156081 A1 | 4/2017 |
| EP | 3473259 A1 | 4/2019 |

(Continued)

OTHER PUBLICATIONS

Freimark et al., Transfusion Medicine and Hemotherapy, 2010;37: 66-73 (Year: 2010).*
English Translation of WO 2017/126612 (Year: 2017).*
Snyder Filtration, 2 pages, retrieved from the internet (Apr. 28, 2021): https://synderfiltration.com/learning-center/articles/membranes/molecular-weight-cut-off/#:~:text=Molecular%20weight%20cut%2Doff%20(MWCO,is%20retained%20by%20the%20membrane. (Year: 2021).*
UF Membrane Pore Size, Microfiltration, 10 pages, retreived from the internet: https://line.17qq.com/articles/olpnkhopv.html (Year: 2021).*
Morris et al., Trends Biotechnol, 1996; 14(5): 163-167 (Year: 1996).*

(Continued)

*Primary Examiner* — Evelyn Y Pyla
(74) *Attorney, Agent, or Firm* — Birch, Stewart, Kolasch & Birch, LLP

(57) ABSTRACT

An object of the present invention is to provide an angiogenic agent that can sufficiently exhibit an angiogenic effect due to mesenchymal stem cells in a state where the angiogenic agent does not allow permeation of host cells while being protected from immune rejection, and a method for method for manufacturing the same. According to the present invention, an angiogenic agent including a mesenchymal stem cell (A); and an immunoisolation membrane (B) that encloses the mesenchymal stem cell is provided.

12 Claims, 17 Drawing Sheets

Specification includes a Sequence Listing.

(56) References Cited

FOREIGN PATENT DOCUMENTS

| | | | |
|---|---|---|---|
| EP | 3646895 A1 | 5/2020 | |
| JP | 5-504704 A | 7/1993 | |
| JP | 7-508187 A | 9/1995 | |
| JP | 10-507111 A | 7/1998 | |
| JP | 2003-190259 A | 7/2003 | |
| JP | 2004-267562 A | 9/2004 | |
| JP | 2008-541953 A | 11/2008 | |
| JP | 2009-7321 A | 1/2009 | |
| JP | 2009-112233 A | 5/2009 | |
| JP | 5290281 B2 | 9/2013 | |
| JP | 2014-12114 A | 1/2014 | |
| JP | 2014-512238 A | 5/2014 | |
| JP | 5606008 B2 | 10/2014 | |
| JP | 2016-516827 A | 6/2016 | |
| JP | 2016-138092 A | 8/2016 | |
| JP | 2017-502008 A | 1/2017 | |
| WO | WO 2011/108517 A1 | 9/2011 | |
| WO | WO 2014/173441 A1 | 10/2014 | |
| WO | WO 2017/023379 A1 | 2/2017 | |
| WO | WO-2017126612 A1 * | 7/2017 | ............ B01D 71/76 |
| WO | WO 2018/088451 A1 | 5/2018 | |
| WO | WO 2018/088452 A1 | 5/2018 | |

OTHER PUBLICATIONS

Word Hippo Thesaurus, Semipermeable Synonyms, retrieved from the internet Nov. 2, 2021: https://www.wordhippo.com/what-is/another-word-for/semipermeable.html#:~:text=Of%20or%20relating%20to%20substance,porous (Year: 2021).*

Grégoire et al., "Review article: mesenchymal stromal cell therapy for inflammatory bowel diseases", Aliment Pharmacol Ther, 2017, vol. 45, pp. 205-221 (17 pages).

International Preliminary Report on Patentability, dated Mar. 12, 2020, and English translation of the Written Opinion of the International Searching Authority, dated Apr. 12, 2018, (Forms PCT/IB/326, PCT/IB/373, and PCT/ISA/237) for International Application No. PCT/JP2018/032162.

International Search Report (Form PCT/ISA/210) for International Application No. PCT/JP2018/032162, dated Dec. 4, 2018, with English translation.

Sakata et al., "Effectiveness of capsulated islet with increased myelocyte", Research Report of the Uehara Memorial Foundation, 2012, vol. 26, 1-4 (4 pages).

Veriter et al., "The impact of hyperclycemia and the presence of encapsulated islets on oxygenation within a bioartificial pancreas in the presence of mesenchymal stem cells in a diabetic Wister rat model", Biomaterials, 2011, vol. 32, pp. 5945-5956 (12 pages).

Brauker et al., "Neovascularization of synthetic membranes directed by membrane microarchitecture", Journal of Biomedical Materials Research, vol. 29, 1995, pp. 1517-1524.

Extended European Search Report dated Sep. 23, 2020 for corresponding Application No. 18852088.6.

Risbud et al., "Islet immunoisolation: experience with biopolymers", J. Biomater. Sci. Polymer Edn., vol. 12, No. 11, 2001, pp. 1243-1252, XP008009610.

International Preliminary Report on Patentability and Written Opinion of the International Searching Authority(Forms PCT/IB/326, PCT/IB/373 and PCT/ISA/237), dated Mar. 12, 2020, for International Application No. PCT/JP2018/032161, with an English Translation.

International Search Report (Form PCT/ISA/210), dated Dec. 4, 2018, for International Application No. PCT/JP2018/032161, with an English translation.

Tatarkiewicz et al., "Reversal Of Hyperglycemia In Mice After Subcutaneous Transplantation Of Macroencapsulated Islets", Transplantation, Mar. 15, 1999, vol. 67, No. 5, pp. 665-671 (10 pages).

Japanese Office Action, dated Dec. 22, 2020, for Japanese Application No. 2019-539624, with an English machine translation.

Japanese Office Action, dated Dec. 22, 2020, for Japanese Application No. 2019-539625, with an English machine translation.

Extended European Search Report, dated Jul. 28, 2020, for European Application No. 18852677.6.

Japanese Office Action, dated Jun. 22, 2021, for Japanese Application No. 2019-539624, with an English machine translation.

Shinmura, "The Fifth Edition of Kojien," Iwanami Shotan, Nov. 11, 1998, pp. 1413 (total 3 pages).

Chinese Office Action and Search Report, dated Jul. 13, 2021 for Chinese Patent Application No. 201880056280.4, with an English translation of the Chinese Office Action.

David et al., "Immunoisolation to Prevent Tissue Graft Rejection: Current Knowledge and Future Use," Experimental Biology and Medicine, vol. 241, 2016 (May 30, 2016), pp. 955-961.

Zeng et al., "Immunoisolation Materials and Methods in Cell Transplantation and Bioartificial Organs," Chinese J. of Dialysis and Artificial Organs, vol. 11, No. 2, 2000 (Jun. 30, 2000), pp. 43-50.

Office Action dated Oct. 1, 2021 in copending U.S. Appl. No. 16/805,075.

Chakrabarty et al., "Preparation, characterization and performance studies of polysulfone membranes using PVP as an additive," Journal of Membrane Science, vol. 315, 2008 (Available online Feb. 21, 2008), pp. 36-47.

Guo et al., "Ultrafitration and its Applications to Sampling and Characterisation of Aquatic Colloids," Environmental Colloids and Particles, vol. 10, Ch. 4, 2007, pp. 159-209 (56 pages total).

Schweicher et al., "Membranes to achieve immunoprotection of transplanted islets,"Front Biosci (Landmark Ed)., vol. 19, Available on Nov. 13, 2014, pp. 49-76 (53 pages total).

U.S. Office Action for U.S. Appl. No. 16/805,075, dated Dec. 21, 2021.

Chinese Office Action for Chinese Application No. 201880056321.X, dated Mar. 9, 2022, with English translation.

Ho et al., "Increased Survival and Function of Mesenchymal Stem Cell Spheroids Entrapped in Instructive Alginate Hydrogels," Stem Cells Translational Medicine, vol. 5, 2016, pp. 773-781, 10 pages total.

Japanese Notification of Reasons for Rescission for Japanese Patent No. 6854904, dated Feb. 3, 2022, with an English translation.

Sumi, "Studies on subcutaneous transplantation therapy for diabetes using mesenchymal stem cells," Grant-in-Aid for Scientific Research, Report of Final Research Achievement, Jun. 15, 2016, Institution No. 14301, 7 pages total, search on Jan. 12, 2022 [online], with an English abstract.

Wang et al., "The paracrine effects of adipose-derived stem cells on neovascularization and biocompatibility of a macroencapsulaiion device," Acta Biomaterialia, vol. 15, 2015, pp. 65-76, 13 pages total. China Academic Journal Electronic Publishing House, Chinese J. Dial & Artif. Organs, vol. 11, No. 2, 2000, pp. 43-50.

Office Action dated Aug. 17, 2021 in corresponding Chinese Patent Application No. 201880056321.X, with English translation.

Chinese Office Action and Search Report for corresponding Chinese Application No. 201880056280.4, dated Jan. 25, 2022, with English translation.

Notice of Allowance issued in U.S. Appl. No. 16/805,075 dated May 13, 2022.

U.S. Notice of Allowance for U.S. Appl. No. 16/805,075, dated Apr. 13, 2022.

* cited by examiner

FIG. 1
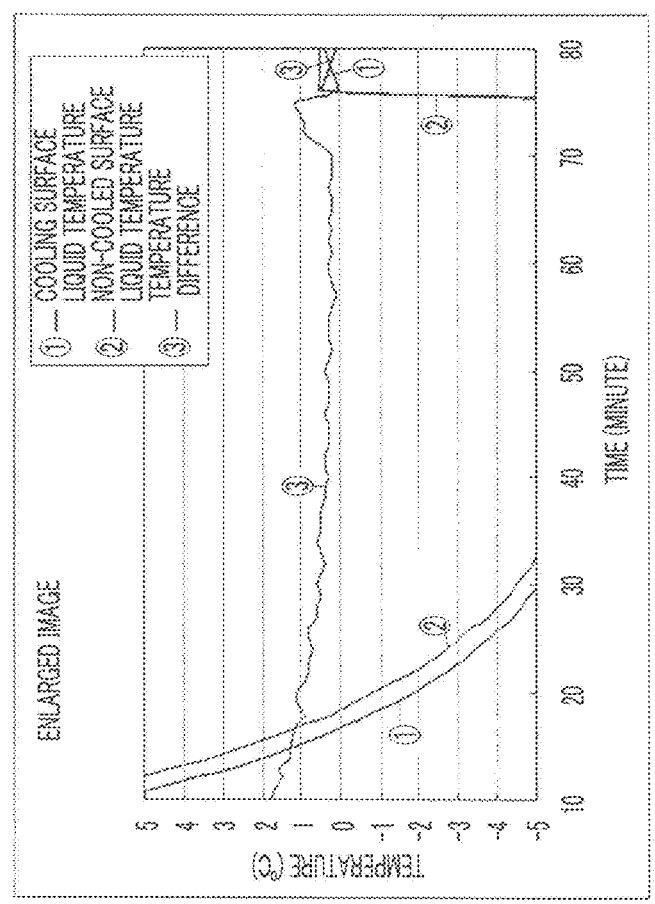
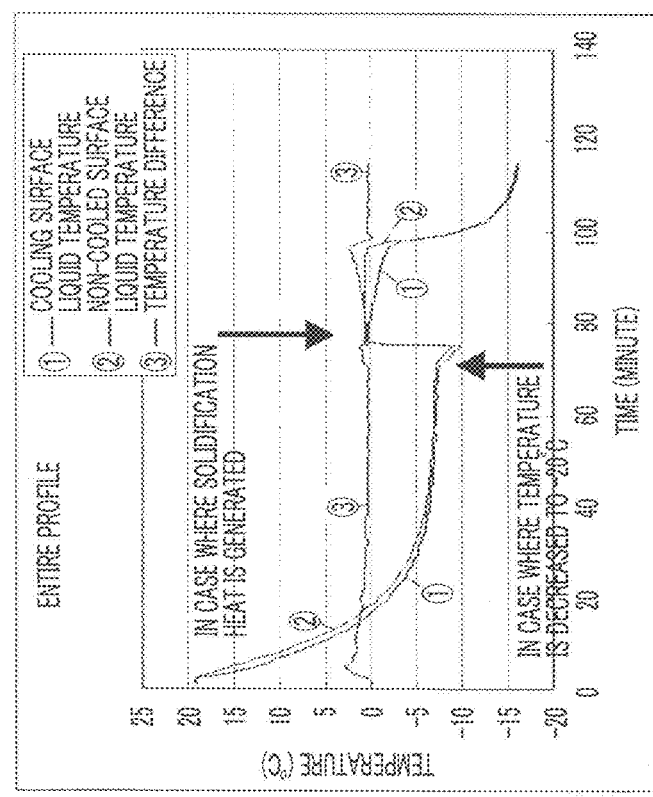

FIG. 2
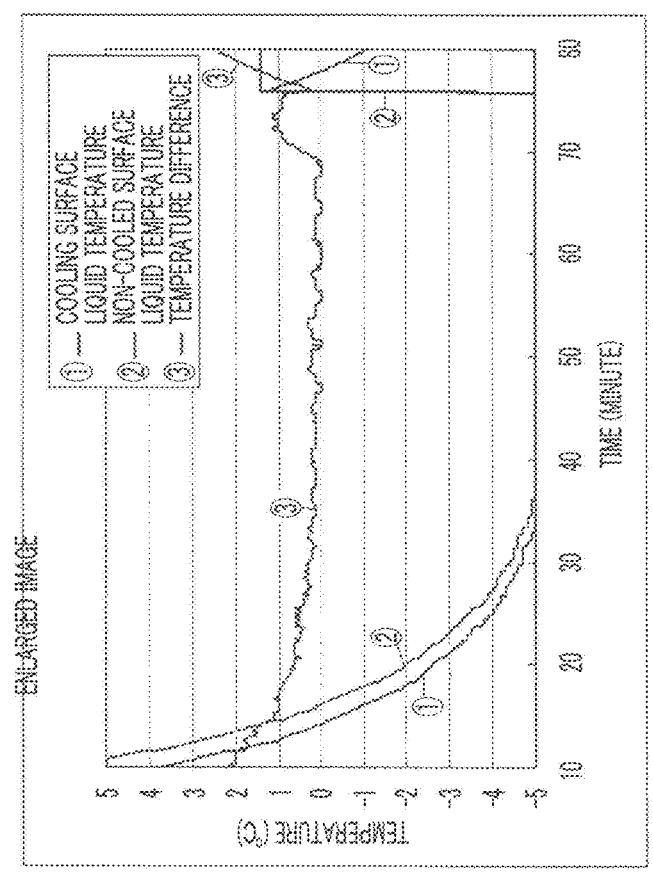
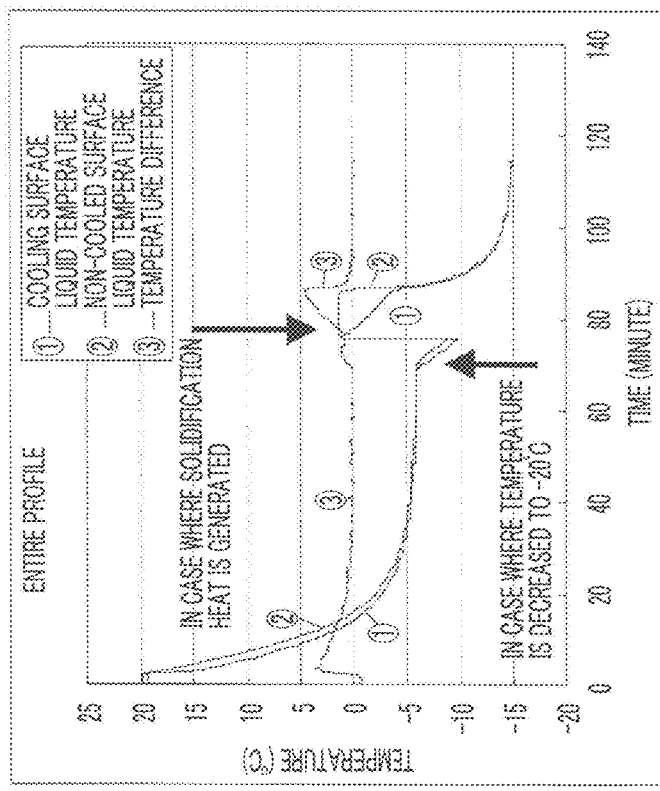

Fig.7
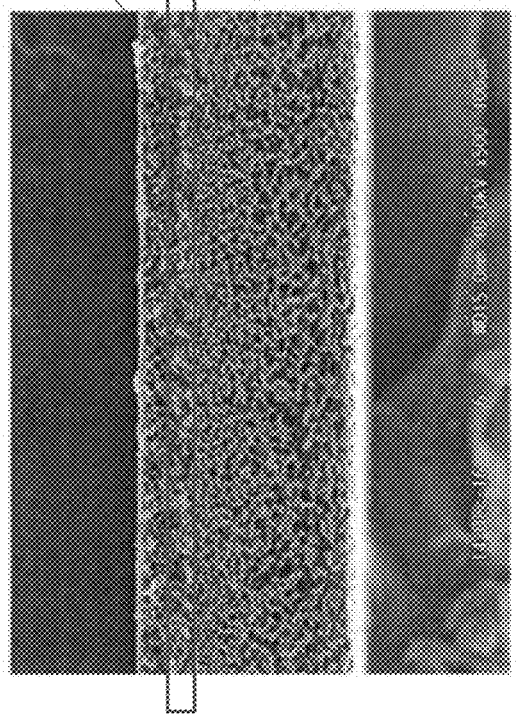
The membrane surface area is not a compact portion.
Compact portion which is located inside the porous membrane and is not in contact with the membrane surface.
Continuous increase in pore diameter in the thickness direction toward the surface
It can be seen that the compact portion is not in contact with the surface portion of the membrane.
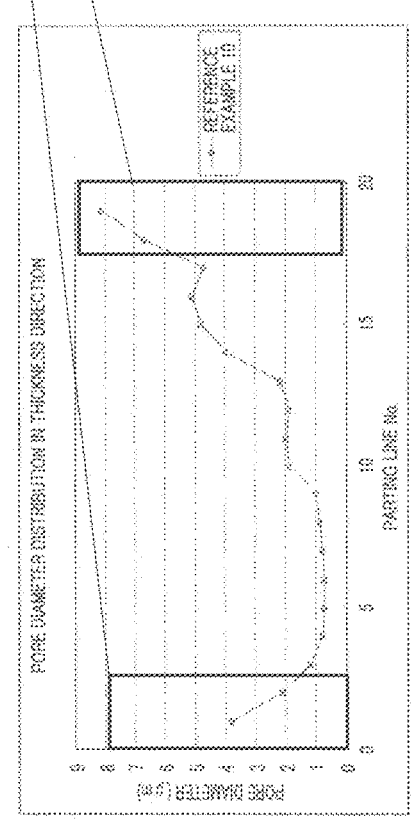
FIG. 8

ANGIOGENIC AGENT AND METHOD OF MANUFACTURING THE SAME

CROSS-REFERENCE TO RELATED APPLICATIONS

This application is a Continuation of PCT International Application No. PCT/JP2018/032162 filed on Aug. 30, 2018, which claims priority under 35 U.S.C § 119(a) to Japanese Patent Application No. 2017-165416 filed on Aug. 30, 2017 and Japanese Patent Application No. 2018-032351 filed on Feb. 26, 2018. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2870-0748PUS 1_ST25.txt" created on Apr. 15, 2020 and is 12,275 bytes in size. The sequence listing contained in this .txt file is part of the specification and is hereby incorporated by reference herein in its entirety.

BACKGROUND OF THE INVENTION

1. Field of the Invention

The present invention relates to an angiogenic agent including a mesenchymal stem cell and an immunoisolation membrane enclosing the mesenchymal stem cell. The present invention further relates to a method for manufacturing an angiogenic agent.

2. Description of the Related Art

Recently, research on regenerative medicine and cell treatment using mesenchymal stem cells (MSC) has been actively conducted. For example, in JP2009-007321A, a method for preventing/treating inflammatory bowel disease by intravenously administering MSC is disclosed. Several clinical studies and clinical trials also have been conducted. However, it has been found that a practically sufficient therapeutic effect cannot be exhibited (Aliment Pharmacol Ther 2017; 45: 205-221). In addition, JP2016-138092A discloses a method for treating a liver disease by administering MSCs cultured in low oxygen. Furthermore, JP5606008B discloses that MSCs cultured in a simulated microgravity environment are suitable for treating central nervous system diseases. Furthermore, angiogenesis use applications for ischemic diseases have been extensively studied, and for example, JP5290281B discloses a therapeutic agent for ischemic limb diseases which includes adipose-derived mesenchymal stem cells.

In consideration of industrial use, there is a problem of acquiring MSCs industrially. As a solution to this problem, using cells of other persons (allogeneic cells) instead of cells of a patient himself or herself is said to be realistic, and many studies using allogeneic MSCs have been carried out in actual clinical studies and clinical trials. However, similar to the problem in organ transplantation from the past, in treatment using allogeneic cells, there is a major problem of transplanted allogeneic MSCs being rejected and eliminated due to immune reaction of a patient himself or herself. MSCs themselves are said to have a property by which the MSCs are relatively unlikely to be rejected by the immune system, but in reality, it is obvious that the MSCs are rejected, and they are eliminated from a body over time. Using an immunosuppressant agent in combination is one solution as in the case of organ transplantation. However, side effects due to the immunosuppressant agent and permanent use thereof are a heavy burden, and therefore it is not a desirable solution.

Accordingly, there is a demand for a method for evading an immune reaction without using an immunosuppressant agent. As one method, a selectively permeable membrane called an immunoisolation membrane has been studied as a device for pancreatic islet transplantation which is assumed to be mainly used for treating diabetes. For example, JP1995-508187A (JP-H07-508187A) discloses an immunoisolation membrane device for transplanting a pancreatic islet that produces insulin, but the document does not disclose a method for transplanting MSCs.

In addition, JP2008-541953A discloses an implantable device that provides a bioactive substance to a subject in need thereof, the device including a microvascular structure in contact with a biocompatible semipermeable pouch that encapsulates one or more kinds of cell capable of producing a bioactive substance. The device of JP2008-541953A is for improving viability and function of transplanted cells, and the document discloses that the device may be an immunoisolation device.

SUMMARY OF THE INVENTION

An object of the present invention is to provide an angiogenic agent that can sufficiently exhibit an angiogenic effect due to mesenchymal stem cells in a state where the angiogenic agent does not allow permeation of host cells while being protected from immune rejection, and a method for method for manufacturing the same.

As a result of intensive studies to achieve the above-described object, the inventors of the present invention have found that, by using an immunoisolation membrane that encloses mesenchymal stem cells, it is possible to provide an angiogenic agent that can sufficiently exhibit an angiogenic effect due to the mesenchymal stem cells in a state where the angiogenic agent is protected from immune rejection, and therefore have completed the present invention.

That is, according to the present invention, the following inventions are provided.

(1) An angiogenic agent comprising: a mesenchymal stem cell (A); and an immunoisolation membrane (B) that encloses the mesenchymal stem cell.

(2) The angiogenic agent according to (1), in which the mesenchymal stem cell is an adipose-derived mesenchymal stem cell or a bone-marrow-derived mesenchymal stem cell.

(3) The angiogenic agent according to (1) or (2), in which the immunoisolation membrane is a porous membrane including a polymer.

(4) The angiogenic agent according to (3), in which a minimum pore diameter of the porous membrane is 0.02 μm to 1.5 μm.

(5) The angiogenic agent according to (3) or (4), in which a thickness of the porous membrane is 10 μm to 250 μm.

(6) The angiogenic agent according to any one of (3) to (5), in which, within an inner side of the porous membrane, a layered compact portion in which a pore diameter is minimized is present, and a pore diameter continuously increases in a thickness direction from the compact portion toward at least one surface of the porous membrane.

(7) The angiogenic agent according to (6), in which a thickness of the compact portion is 0.5 µm to 30 µm.

(8) The angiogenic agent according to any one of (3) to (7), in which a ratio of a maximum pore diameter to a minimum pore diameter of the porous membrane is 3.0 to 20.0.

(9) The angiogenic agent according to any one of (3) to (8), in which the porous membrane contains at least one kind of polysulfone and polyvinylpyrrolidone.

(10) The angiogenic agent according to any one of (1) to (9), in which the mesenchymal stem cell is contained as a cell structure which includes a plurality of biocompatible polymer blocks and a plurality of mesenchymal stem cells of at least one type, and in which at least one of the biocompatible polymer blocks is disposed in gaps between the plurality of mesenchymal stem cells.

(11) The angiogenic agent according to (10), in which a size of one of the biocompatible polymer blocks is 20 µm or more and 200 µm or less.

(12) The angiogenic agent according to (10) or (11), in which in the biocompatible polymer block, a biocompatible polymer is cross-linked by heat, ultraviolet rays, or an enzyme.

(13) The angiogenic agent according to any one of (10) to (12), in which the biocompatible polymer block has an amorphous shape.

(14) The angiogenic agent according to any one of (10) to (13), in which the cell structure includes 0.0000001 µg to 1 µg of biocompatible polymer blocks per cell.

(15) A method for manufacturing the angiogenic agent according to any one of (1) to (14), the method comprising a step of enclosing mesenchymal stem cells with an immunoisolation membrane.

Furthermore, according to the present invention, the following inventions are provided.

(16) An angiogenesis method comprising a step of transplanting, to a subject in need of angiogenesis, a cell transplant device including a mesenchymal stem cell (A) and an immunoisolation membrane (B) that encloses the mesenchymal stem cell.

(17) A cell transplant device which is used for angiogenesis procedure, the device comprising a mesenchymal stem cell (A); and an immunoisolation membrane (B) that encloses the mesenchymal stem cell.

(18) Use of a cell transplant device to manufacture an angiogenic agent, in which the cell transplant device includes a mesenchymal stem cell (A); and an immunoisolation membrane (B) that encloses the mesenchymal stem cell.

SUMMARY OF THE INVENTION

The angiogenic agent of the present invention is useful for promoting angiogenesis by transplanting allogeneic or xenogeneic mesenchymal stem cells (MSCs) which cause immune rejection. According to the present invention, an angiogenic effect due to MSCs can be sufficiently exhibited while protecting the MSCs from host cells. Furthermore, according to the present invention, new blood vessels can be locally generated around the angiogenic agent at a high efficiency.

BRIEF DESCRIPTION OF THE DRAWINGS

FIG. 1 illustrates a liquid temperature profiling of an experiment described in Condition A.

FIG. 2 illustrates a liquid temperature profiling of an experiment described in Condition B.

FIG. 7 illustrates a SEM photograph of a cross section of a porous membrane of Reference Example 10.

DESCRIPTION OF THE PREFERRED EMBODIMENTS

Figure 3:
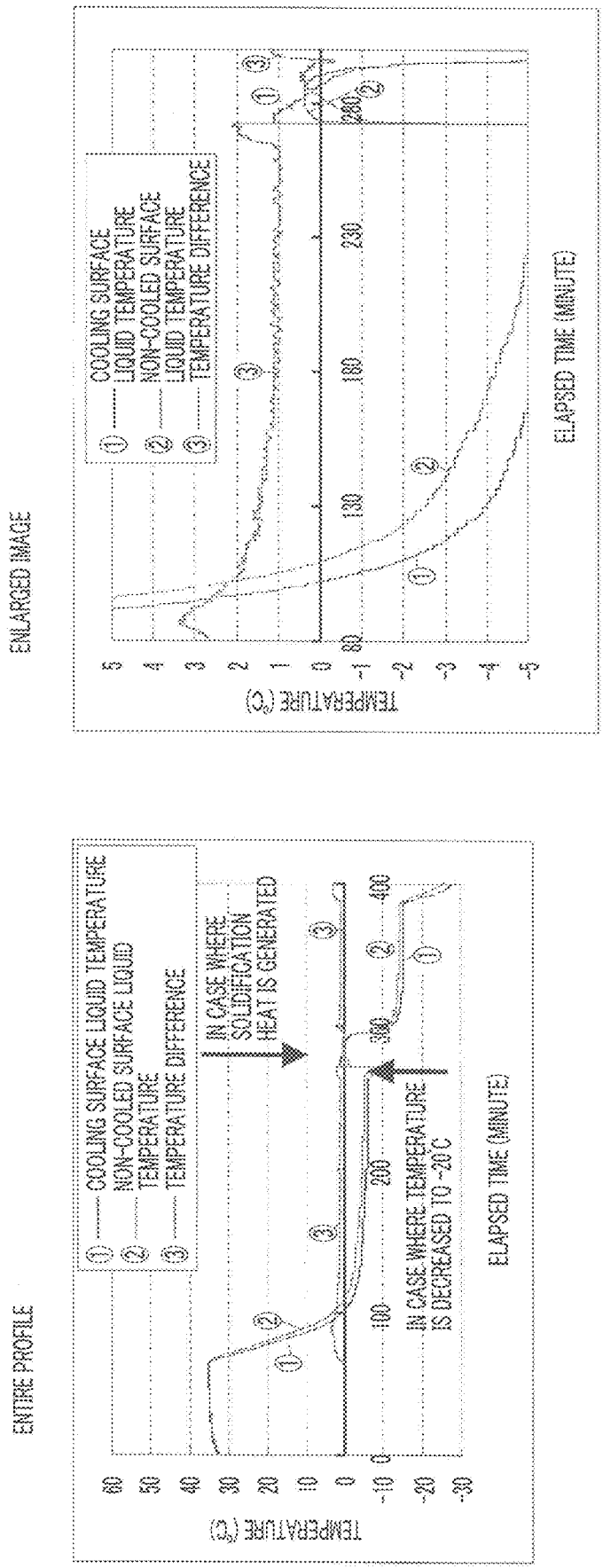
FIG. 3 illustrates a liquid temperature profiling of an experiment described in Condition C.

Hereinafter, embodiments for implementing the present invention are specifically described. The expression "to" in the present specification refers to a range including numerical values described before and after the expression as a minimum value and a maximum value, respectively.

An angiogenic agent of the embodiment of the present invention includes a mesenchymal stem cell (A), and an immunoisolation membrane (B) that encloses the mesenchymal stem cell.

The angiogenic agent of the embodiment of the present invention can locally generate new blood vessels around the angiogenic agent, and can exert a long-term therapeutic effect due to transplanted cells. The angiogenic agent of the embodiment of the present invention itself does not include microvessels, and is different in this respect from the device disclosed in JP2008-541953A. In consideration of industrial use, it is realistic to transplant cells or tissues of other persons. However, in the component of JP2008-541953A, a microvessel itself is a target of rejection due to immune reaction of a host. This is particularly noticeable in a case where a microvessel includes cells, and in consideration of this phenomenon, JP2008-541953A discloses use of allogeanic/syngeneic animals. However, allogeanic/syngeneic animals are established only between animals genetically controlled as experimental animals, and in practice, for example, there is no syngeneic persons in a case of targeting humans, and therefore the component of this document cannot be used. On the other hand, the angiogenic agent of the present invention is greatly different in that it can be used without such restrictions because it does not contain externally-derived microvessel, and a new blood vessel is created by host cells.

<Cell>

Cells used in the present invention are mesenchymal stem cells (MSCs). The origin of the mesenchymal stem cells is not particularly limited, but adipose-derived mesenchymal stem cells or bone-marrow-derived mesenchymal stem cells are preferable, and adipose-derived mesenchymal stem cells are more preferable. A mesenchymal stem cell refers to a somatic stem cell present in the mesenchymal tissue and has an ability to differentiate into a cell belonging to the mesenchymal tissue. The mesenchymal tissue refers to tissues such as bone, cartilage, fat, blood, bone marrow, skeletal muscle, dermis, ligament, tendon, heart, and the like.

<Cell Structure>

The cells used in the present specification may be used as they are, but they may be used as a cell structure. The cell structure referred to in the present invention is a cell structure which includes a plurality of the biocompatible polymer blocks and a plurality of cells of at least one type and in which at least one of the biocompatible polymer blocks is disposed in gaps between the plurality of cells. In the present specification, a cell structure is referred to as a mosaic cell cluster (cell cluster formed in a mosaic pattern) in some cases.

(1) Biocompatible Polymer Block (1-1) Biocompatible Polymer

Biocompatibility means that a remarkable adverse reaction such as a long-term and chronic inflammatory reaction is not caused upon contact with a living body. Regarding the biocompatible polymer used in the present invention, whether to be decomposed within a living body is not particularly limited as long as the biocompatible polymer has an affinity for the living body. However, a biodegradable polymer is preferable. Specific examples of a non-biodegradable material include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of a biodegradable material include a polypeptide (for example, gelatin described below) such as a naturally occurring peptide, a recombinant peptide, or a chemically synthesized peptide, polylactic acid, polyglycolic acid, poly (lactic-co-glycolic acid) (PLGA), hyaluronic acid, glycosaminoglycan, proteoglycan, chondroitin, cellulose, agarose, carboxymethyl cellulose, chitin, and chitosan. Among these, a recombinant peptide is particularly preferable. The biocompatible polymers may be devised to improve cell adhesiveness. Specifically, a method such as "coating a substrate surface with cell adhesion stroma (fibronectin, vitronectin, or laminin) or a peptide having cell adhesion sequence (an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, all expressed as one letter code of amino acids)", "amination and cationization of a substrate surface", or "a plasma treatment and a hydrophilic treatment due to corona discharge on a substrate surface" can be used.

The type of a polypeptide including a recombinant peptide or a chemically synthesized peptide is not particularly limited as long as the polypeptide has biocompatibility. For example, gelatin, collagen, atelocollagen, elastin, fibronectin, pronectin, laminin, tenascin, fibrin, fibroin, entactin, thrombospondin, and RETRONECTIN (registered trademark) are preferable, and gelatin, collagen, and atelocollagen are most preferable. Gelatin to be used in the present invention is preferably natural gelatin, recombinant gelatin, or chemically synthesized gelatin, and more preferably recombinant gelatin. The natural gelatin referred to herein means gelatin produced using naturally derived collagen.

The chemically synthesized peptide and the chemically synthesized gelatin mean an artificially synthesized peptide and artificially synthesized gelatin, respectively. A peptide such as gelatin may be synthesized by solid phase synthesis or liquid phase synthesis, but the solid phase synthesis is preferable. The solid phase synthesis of the peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. As the preferred embodiment of the chemically synthesized gelatin, the contents described in the recombinant gelatin described below in the present specification can be applied.

A "1/IOB" value which is a hydrophilicity value of the biocompatible polymer is preferably 0 to 1.0. The 1/IOB value is more preferably 0 to 0.6 and still more preferably 0 to 0.4. IOB is an index of hydrophilicity and hydrophobicity based on an organic conceptual diagram showing polarity and non-polarity of an organic compound, which has been proposed by Atsushi FUJITA, and the details thereof are described in, for example, "Pharmaceutical Bulletin", Vol. 2, 2, pp. 163 to 173 (1954), "Area of Chemistry", Vol. 11, 10, pp. 719 to 725 (1957), and "Fragrance Journal", Vol. 50, pp. 79 to 82 (1981). Briefly, assuming that the source of all organic compounds is methane ($CH_4$) and all other compounds are derivatives of methane, predetermined numerical values are set for the number of carbon atoms, a substituent, a transformation portion, a ring, and the like of the compounds, scores thereof are added to determine an organic value (OV) and an inorganic value (IV), and these values are plotted on a diagram in which the organic value is placed on an X-axis and the inorganic value is placed on a Y-axis. IOB in the organic conceptual diagram refers to a ratio of the inorganic value (IV) to the organic value (OV) in the organic conceptual diagram, that is, "inorganic value (IV)/organic value (OV)". For the details of the organic conceptual diagram, "New Edition Organic Conceptual Diagram-Foundation and Application-" (written by Yoshio KOUDA et al., Sankyo Shuppan Co., Ltd., 2008) can be referred to. In the present specification, the hydrophilicity and hydrophobicity are represented by a "1/IOB" value obtained by taking a reciprocal of IOB. A smaller "1/IOB" value (close to 0) indicates higher hydrophilicity.

It is presumed that since hydrophilicity becomes high and water absorbency becomes high by setting the "1/IOB"

value of the biocompatible polymer used in the present invention in the above range, the polymer effectively acts to retain nutrient components and, as a result, contributes to the stabilization and viability of cells in the cell structure (mosaic cell cluster) according to the present invention.

In a case where the biocompatible polymer is a polypeptide, the hydrophilicity and hydrophobicity index represented by a grand average of hydropathicity (GRAVY) value is preferably −9.0 to 0.3 and more preferably −7.0 to 0.0. The grand average of hydropathicity (GRAVY) value can be obtained by methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571 to 607" and "Gasteiger E., Gattiker A., Hoogland C., Ivanyi I., Appel R. D., Bairoch A.; ExPASy: the proteomics server for in-depth protein knowledge and analysis; Nucleic Acids Res. 31:3784-3788 (2003)".

It is presumed that since hydrophilicity becomes high and water absorbency becomes high by setting the GRAVY value of the biocompatible polymer in the above range, the polymer effectively acts to retain nutrient components and, as a result, contributes to the stabilization and viability of cells in the cell structure (mosaic cell cluster) according to the present invention.

(1-2) Cross-Linking

The biocompatible polymers may be or may not be cross-linked, but are preferably cross-linked. By using the cross-linked biocompatible polymers, it is possible to obtain an effect of preventing instant decomposition thereof at the time of culturing in a medium and at the time of transplantation into a living body. As general cross-linking methods, thermal cross-linking, cross-linking using aldehydes (for example, formaldehyde, glutaraldehyde, or the like), cross-linking using a condensation agent (carbodiimide, cyanamide, or the like), enzymatic cross-linking, photo cross-linking, ultraviolet cross-linking, a hydrophobic interaction, hydrogen bonding, an ionic interaction, and the like are known, and the cross-linking methods can be used in the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, the enzyme is not particularly limited as long as the enzyme has a function of cross-linking polymer materials. However, it is possible to perform cross-linking preferably using transglutaminase and laccase, and most preferably using transglutaminase. Specific examples of proteins which are enzymatically cross-linked by transglutaminase are not particularly limited as long as the proteins have a lysine residue and a glutamine residue. Transglutaminase may be derived from a mammal or a microorganism. Specific examples thereof include ACTIVA series manufactured by Ajinomoto Co., Inc., mammal-derived transglutaminase which is sold as a reagent, for example, guinea pig liver-derived transglutaminase, goat-derived transglutaminase, and rabbit-derived transglutaminase, which are manufactured by Oriental Yeast Co., Ltd., Upstate USA Inc., and Biodesign International Inc., and human-derived blood coagulation factor (Factor XIIIa, Haematologic Technologies, Inc.).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., particularly preferably 100° C. to 250° C., and most preferably 120° C. to 200° C.

(1-3) Recombinant Gelatin

The recombinant gelatin referred to in the present invention means a polypeptide or a protein-like substance which is produced by gene recombination technology and has an amino acid sequence similar to that of gelatin. The recombinant gelatin which can be used in the present invention preferably has repetition of a sequence represented by Gly-X-Y (X and Y each independently represent any amino acid) which is characteristic of collagen. Herein, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen. For example, it is possible to use recombinant gelatin disclosed in EP1014176, U.S. Pat. No. 6,992,172B, WO2004/085473A, and WO2008/103041A, but the present invention is not limited thereto. A preferred example of the recombinant gelatin used in the present invention is recombinant gelatin of the following aspect.

The recombinant gelatin is excellent in biocompatibility due to original characteristics of natural gelatin, is not naturally derived so that there is no concern about bovine spongiform encephalopathy (BSE) or the like, and is excellent in non-infection properties. The recombinant gelatin is more uniform than natural gelatin, and a sequence thereof is determined. Accordingly, it is possible to precisely design the strength and degradability with less fluctuation due to cross-linking or the like.

The molecular weight of the recombinant gelatin is not particularly limited, and is preferably 2,000 to 100,000 (2 kilodaltons (kDa) to 100 kDa), more preferably 2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has repetition of a sequence represented by Gly-X-Y which is characteristic of collagen. Herein, a plurality of pieces of Gly-X-Y may be the same as or different from each other. In Gly-X-Y, Gly represents glycine and X and Y represent any amino acid (preferably represents any amino acid other than glycine). The sequence represented by Gly-X-Y which is characteristic of collagen is a partial structure which is extremely specific in a sequence and a composition of an amino acid of gelatin and collagen, compared with other proteins. In this portion, glycine occupies about one third of the entire sequence, and is repeated at every third position in an amino acid sequence. Glycine is the simplest amino acid, has little restraint on the arrangement of the molecular chains, and significantly contributes to regeneration of a helix structure during gelation. It is preferable that amino acids represented by X and Y contain many imino acids (proline and oxyproline) and occupy 10% to 45% of the entire sequence. Preferably 80% or more, more preferably 95% or more, and most preferably 99% or more of the amino acids in the sequence of the recombinant gelatin have a repeating structure of Gly-X-Y.

In general gelatin, a polar charged amino acid and a polar uncharged amino acid are present at a ratio of 1:1. Herein, the polar amino acid specifically indicates cysteine, aspartic acid, glutamic acid, histidine, lysine, asparagine, glutamine, serine, threonine, tyrosine, and arginine. Among these, the polar uncharged amino acid indicates cysteine, asparagine, glutamine, serine, threonine, and tyrosine. In the recombinant gelatin used in the present invention, the proportion of the polar amino acid in the whole constituent amino acid is 10% to 40% and is preferably 20% to 30%. The proportion of the uncharged amino acid in the polar amino acids is greater than or equal to 5% and less than 20% and is preferably greater than or equal to 5% and less than 10%. It is preferable that any one amino acid or preferably two or more amino acids among serine, threonine, asparagine, tyrosine, and cysteine are not contained on the sequence.

In general, a minimum amino acid sequence which functions as a cell adhesion signal in a polypeptide is known (for example, Nagai Shoten Co., Ltd., "Pathophysiology", Vol. 9, No. 7 (1990), p. 527). The recombinant gelatin used in the present invention preferably has two or more cell adhesion signals in one molecule. As the specific sequence, sequences such as an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are expressed as one letter code of amino acids, are preferable because many kinds of cells adhere to these sequences. An RGD sequence, a YIGSR sequence (SEQ ID NO: 3), a PDSGR sequence (SEQ ID NO: 4), an LGTIPG sequence (SEQ ID NO: 6), an IKVAV sequence (SEQ ID NO: 8), and a HAV sequence are more preferable, and an RGD sequence is particularly preferable. In the RGD sequences, an ERGD sequence (SEQ ID NO: 10) is preferable. A production amount of stroma of a cell can be improved by using recombinant gelatin having cell adhesion signals.

As the disposition of RGD sequences in the recombinant gelatin, it is preferable that the number of amino acids between RGDs is not uniform between 0 and 100, and it is more preferable that the number of amino acids between RGDs is not uniform between 25 and 60. The content of this minimum amino acid sequence unit is preferably 3 to 50, more preferably 4 to 30, particularly preferably 5 to 20, and most preferably 12 in one molecule of a protein in the viewpoint of cell adhesion and proliferation properties.

In the recombinant gelatin, a proportion of an RGD motif with respect to the total number of amino acids is preferably at least 0.4%. In a case where the recombinant gelatin contains 350 or more amino acids, each stretch of the 350 amino acids preferably contains at least one RGD motif. The proportion of the RGD motif with respect to the total number of amino acids is more preferably at least 0.6%, still more preferably at least 0.8%, even more preferably at least 1.0%, particularly preferably at least 1.2%, and most preferably at least 1.5%. The number of RGD motifs within a recombinant peptide is preferably at least 4, more preferably at least 6, still more preferably at least 8, and particularly preferably 12 to 16 per 250 amino acids. The proportion of the RGD motif of 0.4% corresponds to at least one RGD sequence per 250 amino acids. The number of RGD motifs is an integer, and accordingly, gelatin consisting of 251 amino acids needs to contain at least two RGD sequences in order to satisfy the characteristics of 0.4%. The recombinant gelatin preferably contains at least two RGD sequences per 250 amino acids, more preferably contains at least three RGD sequences per 250 amino acids, and still more preferably contains at least four RGD sequences per 250 amino acids. As another aspect of the recombinant gelatin, the recombinant gelatin preferably contains at least 4 RGD motifs, more preferably contains at least 6 RGD motifs, still more preferably contains at least 8 RGD motifs, and particularly preferably contains 12 to 16 RGD motifs.

The recombinant gelatin may be partially hydrolyzed.

The recombinant gelatin is preferably represented by Formula 1: A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents any amino acid or any amino acid sequence and B represents any amino acid or any amino acid sequence. n pieces of Gly-X-Y may be the same as or different from each other.

More preferably, the recombinant gelatin is represented by Gly-Ala-Pro-[(Gly-X-Y)$_{63}$]$_3$-Gly (SEQ ID NO: 11)(in the formula, 63 pieces of X each independently represent any amino acid and 63 pieces of Y each independently represent any amino acid. 63 pieces of Gly-X-Y may be the same as or different from each other).

It is preferable that a plurality of sequence units of naturally existing collagen are bonded to a repeating unit. The naturally existing collagen referred to herein is not limited as long as the collagen exists naturally, but is preferably I type collagen, II type collagen, III type collagen, IV type collagen, or V type collagen, and more preferably I type collagen, II type collagen, or III type collagen. According to another embodiment, the above-described collagen is derived preferably from a human, cattle, a pig, a mouse, or a rat, and more preferably from a human.

An isoelectric point of the recombinant gelatin is preferably 5 to 10, more preferably 6 to 10, and still more preferably 7 to 9.5. The measurement of the isoelectric point of the recombinant gelatin can be carried out by measuring a pH after passing a 1 mass % gelatin solution through a mixed crystal column of a cation-anion exchange resin, as described in the isoelectric focusing method (refer to Maxey, C. R. (1976); Phitogr. Gelatin 2, Editor Cox, P. J. Academic, London, Engl.).

It is preferable that the recombinant gelatin is not deaminated.

It is preferable that the recombinant gelatin does not have a telopeptide.

It is preferable that the recombinant gelatin is a substantially pure polypeptide prepared using a nucleic acid which encodes an amino acid sequence.

It is particularly preferable that the recombinant gelatin is any of (1) a peptide consisting of an amino acid sequence described in SEQ ID NO: 1;

(2) a peptide which is formed of an amino acid sequence in which one or several amino acids are deleted, substituted, or added in the amino acid sequence described in SEQ ID No: 1, and has biocompatibility; or (3) a peptide which is formed of an amino acid sequence having 80% or more (more preferably 90% or more, particularly preferably 95% or more, and most preferably 98% or more) sequence identity to the amino acid sequence described in SEQ ID No: 1, and has biocompatibility.

The sequence identity in the present invention refers to a value calculated by the following expression.

% Sequence identity=[(the number of identical residues)/(alignment length)]×100

The sequence identity between two amino acid sequences can be determined by any method well-known to those skilled in the art, and can be determined by using a basic local alignment search tool (BLAST) program (J. Mol. Biol. 215: 403 to 410, 1990) or the like.

"One or several" in the expression "amino acid sequence in which one or several amino acids are deleted, substituted, or added" means preferably 1 to 20 amino acids, more preferably 1 to 10 amino acids, still more preferably 1 to 5 amino acids, and particularly preferably 1 to 3 amino acids.

The recombinant gelatin can be produced by a gene recombination technology which is well-known to those skilled in the art, and can be produced, for example, in accordance with methods disclosed in EP1014176A2, U.S. Pat. No. 6,992,172B, WO2004/085473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Accordingly, the recombinant gelatin used in the present invention can be prepared by collecting the recombinant gelatin produced from a culture product.

(1-4) Biocompatible Polymer Block

In the present invention, a block (cluster) formed of the above-described biocompatible polymers can be used.

The shape of the biocompatible polymer block in the present invention is not particularly limited. Examples thereof include an amorphous shape, a spherical shape, a particulate shape (granule), a powdery shape, a porous shape, a fibrous shape, a spindle shape, a flat shape, and a sheet shape, and an amorphous shape, a spherical shape, a particulate shape (granule), a powdery shape, and a porous shape are preferable. The amorphous shape indicates that a shape of a surface is uneven, and indicates, for example, an object having roughness, such as rock. Examples of the above-described shapes are not distinct from each other, and, for example, an amorphous shape is included in an example of a subordinate concept of the particulate shape (granule) in some cases.

The shape of the biocompatible polymer block in the present invention is not particularly limited as described above. However, tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how many blocks can be densely packed in a certain volume, and it is apparent that as the value becomes lower, the blocks cannot be densely packed, that is, the structure of the block is complicated. It is considered that the tap density of the biocompatible polymer block indicates complexity of a surface structure of the biocompatible polymer block and a volume of a void formed in a case where biocompatible polymer blocks are collected as an aggregate. As the tap density becomes smaller, the void between biocompatible polymer blocks becomes larger and a grafted region of a cell becomes larger. In addition, by setting the tap density to be not too small, the biocompatible polymer block can appropriately exist between cells, and in a case where a cell structure is formed, nutrients can be delivered into the cell structure. Therefore, it is considered to be preferable that the tap density falls within the above range.

The measurement of the tap density referred to in the present specification is not particularly limited, but can be performed as follows. A container (having a cylindrical shape with a diameter of 6 mm and a length of 21.8 mm: a capacity of 0.616 cm$^3$) (hereinafter, described as a cap) is prepared for the measurement. First, a mass of only the cap is measured. Then, a funnel is attached to the cap, and blocks are poured from the funnel so as to be accumulated in the cap. After pouring a sufficient amount of blocks, the cap portion is hit 200 times on a hard object such as a desk, the funnel is removed, and the blocks are leveled off with a spatula. A mass is measured in a state where the cap is filled up with the blocks. The tap density can be determined by calculating a mass of only the blocks from the difference between the mass of the cap filled up with the blocks and the mass of only the cap, and dividing the mass of only the blocks by the volume of the cap.

A cross-linking degree of the biocompatible polymer block in the present invention is not particularly limited, but is preferably greater than or equal to 2, more preferably 2 to 30, still more preferably 4 to 25, and particularly preferably 4 to 22.

The method of measuring the cross-linking degree (the number of times of cross-linking per molecule) of the biocompatible polymer block is not particularly limited. However, in a case where the biocompatible polymer is CBE3, the measurement can be performed, for example, by a TNBS (2,4,6-trinitrobenzene sulfonic acid) method described in the following examples. Specifically, a sample obtained by mixing a biocompatible polymer block, a NaHCO$_3$ aqueous solution, and a TNBS aqueous solution, allowing the mixture to react for 3 hours at 37° C., and then stopping the reaction, and a blank obtained by mixing a biocompatible polymer block, a NaHCO$_3$ aqueous solution, and a TNBS aqueous solution and stopping a reaction immediately after the mixing are prepared. Each absorbance (345 nm) of the sample and the blank which are diluted with pure water is measured, and the cross-linking degree (the number of times of cross-linking per molecule) can be calculated from (Expression 2) and (Expression 3).

$$(As-Ab)/14,600 \times V/w \qquad \text{(Expression 2)}$$

(Expression 2) represents an amount (molar equivalent) of lysine per 1 g of the biocompatible polymer block.

(In the expression, As represents a sample absorbance, Ab represents a blank absorbance, V represents an amount (g) of reaction liquid, and w represents a mass (mg) of the biocompatible polymer block.)

$$1-(\text{sample (Expression 2)/uncross-linked polymer (Expression 2)}) \times 34 \qquad \text{(Expression 3)}$$

(Expression 3) represents the number of times of cross-linking per molecule.

A water absorption rate of the biocompatible polymer block in the present invention is not particularly limited, but is preferably greater than or equal to 300%, more preferably greater than or equal to 400%, still more preferably greater than or equal to 500%, particularly preferably greater than or equal to 600%, and most preferably greater than or equal to 700%. An upper limit of the water absorption rate is not particularly limited, but is generally less than or equal to 4,000% or less than or equal to 2,000%.

The method of measuring the water absorption rate of the biocompatible polymer block is not particularly limited. However, the water absorption rate can be measured, for example, by the method described in the following examples. Specifically, a 3 cm×3 cm bag made of nylon mesh is filled with about 15 mg of a biocompatible polymer block at 25° C., is swollen in ion exchange water for 2 hours, and then is dried with air for 10 minutes, the mass thereof is measured at each stage, the water absorption rate is determined according to (Expression 4).

$$\text{Water absorption rate} = (w2 - w1 - w0)/w0 \quad \text{(Expression 4)}$$

(In the expression, w0 represents a mass of a material before water absorption, w1 represents a mass of an empty bag after water absorption, and w2 represents a mass of the whole bag containing the material after water absorption.)

The size of one biocompatible polymer block in the present invention is not particularly limited, but is preferably 20 µm to 200 µm, more preferably 20 µm to 150 µm, still more preferably 50 µm to 120 µm, and particularly preferably 53 µm to 106 µm.

By setting the size of one biocompatible polymer block in the above range, nutrient delivery into a cell structure from the outside can be improved. The size of one biocompatible polymer block does not mean that an average value of the sizes of a plurality of biocompatible polymer blocks is within the above range, but means the size of each biocompatible polymer block which is obtained by sieving a plurality of biocompatible polymer blocks.

The size of one block can be defined by a size of a sieve used in a case of dividing the blocks. For example, blocks remaining on a sieve with 106 µm in a case where blocks which have been passed through a sieve with 180 µm for sifting are sifted using the sieve with 106 µm can be regarded as blocks having a size of 106 to 180 µm. Next, blocks remaining on a sieve with 53 µm in a case where blocks which have been passed through the sieve with 106 µm for sifting are sifted using the sieve with 53 µm can be regarded as blocks having a size of 53 to 106 µm. Next, blocks remaining on a sieve with 25 µm in a case where blocks which have been passed through the sieve with 53 µm for sifting are sifted using the sieve with 25 µm can be regarded as blocks having a size of 25 to 53 µm.

(1-5) Method of Producing Biocompatible Polymer Block

The method of producing a biocompatible polymer block is not particularly limited. For example, it is possible to obtain a biocompatible polymer block by pulverizing a solid matter (such as a porous body of a biocompatible polymer) containing a biocompatible polymer using a pulverizer (such as NEW POWER MILL). The solid matter (such as a porous body) containing a biocompatible polymer can be obtained, for example, by freeze-drying an aqueous solution containing the biocompatible polymer.

By pulverizing the solid matter containing a biocompatible polymer as described above, an amorphous biocompatible polymer block having an uneven surface shape can be produced.

The method of producing the porous body of the biocompatible polymer is not particularly limited, but the porous body can also be obtained by freeze-drying an aqueous solution containing a biocompatible polymer. For example, by including a freezing step in which the liquid temperature (highest internal highest liquid temperature) of a portion having the highest liquid temperature in the solution is lower than or equal to "solvent melting point−3° C." in the unfrozen state, the ice to be formed can have a spherical shape. By drying the ice after performing this step, a porous body having spherical isotropic holes (spherical pores) can be obtained. For example, by performing freezing without including a freezing step in which the liquid temperature (highest internal liquid temperature) of a portion having the highest liquid temperature in the solution is higher than or equal to "solvent melting point−3° C." in the unfrozen state, the ice to be formed can have a pillar/flat plate shape. By drying the ice after performing this step, a porous body having holes (pillars/flat plate pores) with pillar or flat shapes which are long uniaxially or biaxially can be obtained. In a case where the porous body of the biocompatible polymer is pulverized to produce a biocompatible polymer block, the holes of the porous body before pulverization influence the shape of the biocompatible polymer block to be obtained, and thus the shape of the biocompatible polymer block to be obtained can be adjusted by adjusting the condition of freeze-drying as described above.

An example of a method of producing a porous body of a biocompatible polymer includes a method including a step (a) of cooling a solution of biocompatible polymers to an unfrozen state under the conditions where the difference between a temperature of a portion having the highest liquid temperature in the solution and a temperature of a portion having the lowest liquid temperature in the solution is lower than or equal to 2.5° C. and the temperature of the portion having the highest liquid temperature in the solution is lower than or equal to a melting point of a solvent;

a step (b) of freezing the solution of the biocompatible polymers obtained in the step (a); and a step (c) of freeze-drying the frozen biocompatible polymers obtained in the step (b).

However, the present invention is not limited to the above method.

In a case where the solution of the biocompatible polymers is cooled to an unfrozen state, the variation in the sizes of obtained porous pores is reduced by making the difference between the temperature of the portion having the highest liquid temperature and the temperature of the portion having the lowest liquid temperature in the solution be lower than or equal to 2.5° C. (preferably lower than or equal to 2.3° C. and more preferably lower than or equal to 2.1° C.), that is, by reducing the difference in temperature. A lower limit of the difference between the temperature of the portion having the highest liquid temperature and the temperature of the portion having the lowest liquid temperature in the solution is not particularly limited, but may be higher than or equal to 0° C. For example, the lower limit thereof may be higher than or equal to 0.1° C., higher than or equal to 0.5° C., higher than or equal to 0.8° C., or higher than or equal to 0.9° C. Accordingly, the cell structure using the biocompatible polymer block which is produced with the produced porous body achieves the effect of showing a large number of cells.

The cooling in the step (a) is preferably carried out, for example, using a material (preferably TEFLON (registered trademark)) having a lower thermal conductivity than water. The portion having the highest liquid temperature in the solution can be supposed as the farthest portion from a cooling side, and the portion having the lowest liquid temperature in the solution can be supposed as a liquid temperature of the cooled surface.

In the step (a), the difference between the temperature of the portion having the highest liquid temperature in the solution and the temperature of the portion having the lowest liquid temperature in the solution, immediately before generation of solidification heat, is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature is the largest between 1 second and 10 seconds before the generation of solidification heat.

In the step (a), the temperature of the portion having the lowest liquid temperature in the solution is preferably lower than or equal to "solvent melting point−5° C.", more preferably lower than or equal to "solvent melting point−5° C." and higher than or equal to "solvent melting point−20° C.", and still more preferably lower than or equal to "solvent melting point−6° C." and higher than or equal to "solvent melting point−16° C.". The solvent in the solvent melting point refers to a solvent of a solution of biocompatible polymers.

In the step (b), the solution of the biocompatible polymers obtained in the step (a) is frozen. The cooling temperature for the freezing in the step (b) is not particularly limited and depends on cooling equipment. However, the cooling temperature is a temperature which is lower than the temperature of the portion having the lowest liquid temperature in the solution preferably by 3° C. to 30° C., more preferably by 5° C. to 25° C., and still more preferably by 10° C. to 20° C.

In the step (c), the frozen biocompatible polymers obtained in the step (b) are freeze-dried. The freeze-drying can be performed by a usual method. For example, the freeze-drying can be performed by carrying out vacuum drying at a temperature lower than a melting point of a solvent and further carrying out vacuum drying at room temperature (20° C.).

In the present invention, a biocompatible polymer block can be produced preferably by pulverizing the porous body obtained in the above-described step (c).

(2) Cell Structure

The cell structure is a cell structure which includes a plurality of the biocompatible polymer blocks and a plurality of cells of at least one type and in which at least one of the polymer blocks is disposed in gaps between the plurality of cells. The biocompatible polymer blocks and the cells are used and the plurality of polymer blocks are three-dimensionally disposed in a mosaic pattern in the gaps between the plurality of cells. By three-dimensionally disposing the biocompatible polymer blocks and the cells in a mosaic pattern, a three-dimensional cell structure in which cells uniformly exist in the structure is formed and material permeability is obtained.

In the cell structure, the plurality of polymer blocks are disposed in gaps between the plurality of cells. Here, the "gaps between cells" are not necessarily spaces closed by the constituent cells, and may be interposed between the cells. Moreover, gaps are not necessarily present between all of the cells, and there may be a place where the cells are in contact with each other. The distance of a gap between cells through the polymer block, that is, the gap distance in a case of selecting a certain cell and a cell present at the shortest distance from the certain cell is not particularly limited. However, the distance is preferably the same as the size of a polymer block, and a suitable distance is also within a range of a suitable size of a polymer block.

Furthermore, the polymer blocks are configured to be interposed between the cells. However, cells are not necessarily present between all of the polymer blocks, and there may be a place where the polymer blocks are in contact with each other. The distance between polymer blocks through the cell, that is, the distance in a case of selecting a polymer block and a polymer block present at the shortest distance from the polymer block is not particularly limited. However, the distance is preferably the same as a size of a cluster of cells in a case where one or several cells to be used are gathered and for example, the size thereof is 10 μm to 1,000 μm, preferably 10 μm to 100 μm, and more preferably 10 μm to 50 μm.

In the present specification, the expression "uniformly exist" in "three-dimensional cell structure in which cells uniformly exist in the structure" or the like is used, but does not mean complete uniformity.

A thickness or a diameter of the cell structure can be set to a desired size, but a lower limit thereof is preferably greater than or equal to 100 μm, more preferably greater than or equal to 215 μm, still more preferably greater than or equal to 400 μm, and most preferably greater than or equal to 730 μm. An upper limit of the thickness or the diameter is not particularly limited, but a general range thereof in use is preferably less than or equal to 3 cm, more preferably less than or equal to 2 cm, and still more preferably less than or equal to 1 cm. The range of the thickness or the diameter of the cell structure is preferably 100 μm to 3 cm, more preferably 400 μm to 3 cm, still more preferably 500 μm to 2 cm, and even more preferably 720 μm to 1 cm.

In the cell structure, regions including polymer blocks and regions including cells are preferably disposed in a mosaic pattern. Moreover, in the present specification, the expression "the thickness or the diameter of the cell structure" means the followings. In a case where one point A in the cell structure is selected, a length of a line segment which divides the cell structure so that the distance from an outer boundary of the cell structure is the shortest in a straight line passing through the point A is set as a line segment A. The point A at which the line segment A becomes the longest is selected in the cell structure, and a length of the line segment A in this case is set as "a thickness or a diameter of a cell structure".

In the cell structure, a ratio of a polymer block to a cell is not particularly limited. However, a mass of a polymer block per cell is preferably 0.0000001 μg to 1 μg, more preferably 0.000001 μg to 0.1 μg, still more preferably 0.00001 μg to 0.01 μg, and most preferably 0.00002 μg to 0.006 μg. By setting the ratio in the above range, the cells can further uniformly exist. By setting a lower limit thereof in the above range, the effect of the cell can be exhibited in case of using the cell structure for the above-described application, and by setting an upper limit thereof in the above range, components optionally present in the polymer block can be supplied to the cell. Here, the components in the polymer block are not particularly limited, but examples thereof include components contained in a medium described below.

(3) Method of Producing Cell Structure

The cell structure can be produced by mixing biocompatible polymer blocks and at least one type of cells. Specifically, the cell structure can be produced by alternately disposing the biocompatible polymer blocks (cluster including biocompatible polymers) and the cells. Moreover, "alternately" does not mean complete alternation, but for example, means a state where the biocompatible polymer blocks and the cells are mixed. The production method is not particularly limited, but is preferably a method of seeding cells after a polymer block is formed. Specifically, a cell structure can be produced by incubating a mixture of the biocompatible polymer blocks and a cell-containing culture solution. For example, the cells and the biocompatible polymer blocks produced in advance are disposed in a mosaic pattern in a container or in a liquid held in a container. As a means of disposition, it is preferable to promote and control formation of mosaic-like disposition including the cells and the biocompatible polymer blocks by using spontaneous aggregation, natural falling, centrifugation, and stirring.

The container to be used is preferably a container made of a cell low-adhesive material or a cell non-adhesive material, and more preferably a container made of polystyrene, polypropylene, polyethylene, glass, polycarbonate, and polyethylene terephthalate. A shape of a bottom surface of the container is preferably a flat bottom shape, a U shape, or a V shape.

With respect to the mosaic-patterned cell structure obtained by the above method, a cell structure having a desired size can be produced by a method such as (a) fusing mosaic cell clusters which are separately prepared, or (b) increasing a volume thereof in a differentiation medium or a proliferation medium. The method of fusion and the method of increasing a volume are not particularly limited.

For example, in a step of incubating the mixture of the biocompatible polymer blocks and the cell-containing culture solution, the volume of the cell structure can be increased by replacing the medium with a differentiation medium or a proliferation medium. Preferably, in the step of incubating the mixture of the biocompatible polymer blocks and the cell-containing culture solution, a cell structure which has a desired size and in which cells uniformly exist can be produced by further adding the biocompatible polymer blocks.

Specifically, the method of fusing mosaic cell clusters which are separately prepared is a method of producing a cell structure including a step of fusing a plurality of cell structures which include a plurality of biocompatible polymer blocks and a plurality of cells and in which one or the plurality of biocompatible polymer blocks are disposed in a part or all of a plurality of gaps formed by the plurality of cells.

<Immunoisolation Membrane>

In the present specification, an immunoisolation membrane means a membrane used for immunoisolation.

Immunoisolation is a method of preventing immune rejection. In general, immunoisolation is one method of preventing immune rejection of a recipient during transplantation. The immune rejection is the rejection of a recipient to a cell structure to be transplanted. A cell structure is sequestered from immune rejection of a recipient. Examples of immune rejection includes immune rejection occurring due to cellular immune responses, and immune rejection occurring due to humoral immune responses.

The immunoisolation membrane is a selectively permeable membrane that allows nutrients such as oxygen, water, and glucose to permeate therethrough, and inhibits permeation of immune cells and the like involved in an immune rejection. Examples of immune cells include macrophages, dendritic cells, neutrophils, eosinophils, basophils, natural killer cells, various T cells, B cells, and other lymphocytes.

Depending on the application, the immunoisolation membrane preferably inhibits permeation of high-molecular-weight proteins such as immunoglobulins (IgM, IgG, and the like) and complements, and preferably allows a relatively low-molecular-weight physiologically active substances such as insulin to permeate therethrough.

The selective permeability of the immunoisolation membrane may be adjusted according to the application. The immunoisolation membrane may be a selectively permeable membrane which blocks a substance having a molecular weight such as 500 kDa or more, 100 kDa or more, 80 kDa or more, or 50 kDa or more. For example, it is preferable that the immunoisolation membrane be capable of inhibiting permeation of the smallest IgG (molecular weight of about 160 kDa) among antibodies. In addition, the immunoisolation membrane may be a selectively permeable membrane which blocks a substance having a diameter such as 500 nm or more, 100 nm or more, 50 nm or more, or 10 nm or more, as a sphere size.

The immunoisolation membrane preferably includes a porous membrane containing a polymer. The immunoisolation membrane may consist only of a porous membrane containing a polymer, or may include other layers. Examples of other layers include a hydrogel film. The immunoisolation membrane may have a protective film that can be easily peeled off from a surface for transportation or the like.

A thickness of the immunoisolation membrane is not particularly limited. It is sufficient for the thickness thereof to be 10 μm to 500 μm. The thickness thereof is preferably 20 μm to 300 μm, and is more preferably 30 μm to 250 μm.

[Porous Membrane]

(Structure of Porous Membrane)

The porous membrane is a membrane having a plurality of pores. Pores can be checked by, for example, a scanning electron microscope (SEM) image of a cross section of the membrane, or a transmission electron microscope (TEM) image thereof.

A thickness of the porous membrane is not particularly limited, but it is preferably 10 μm to 500 μm, is more preferably 10 μm to 300 μm, and is even more preferably 10 μm to 250 μm.

Preferably, within an inner side of the porous membrane, a layered compact portion in which a pore diameter is minimized is present, and a pore diameter continuously increases in a thickness direction from the compact portion toward at least one surface of the porous membrane. A pore diameter is determined based on an average pore diameter of sections to be described later.

A surface of the membrane means a main surface (a front surface or a back surface indicating an area of the membrane), and does not mean a surface in a thickness direction at the end of the membrane. The surface of the porous membrane may be an interface with another layer. In the immunoisolation membrane, the porous membrane preferably has a uniform structure over the entire area with respect to a pore diameter or pore diameter distribution (a difference in pore diameter in the thickness direction), and the like.

The porous membrane having a pore diameter distribution can prolong the life of the immunoisolation membrane. The reason for this is because of an effect as if multi-stage filtration has been performed using membranes having substantially different pore diameters, and thereby deterioration of the membrane can be prevented.

A pore diameter may be measured from a photograph of a cross section of the membrane obtained by an electron microscope. The porous membrane can be cut with a microtome or the like, and it is possible to obtain a photograph of a cross section of the porous membrane as a section of a thin membrane which a cross section can be observed.

In the present specification, comparison of the pore diameter in the thickness direction of the membrane is performed by dividing the SEM photograph of the cross section of the membrane in the thickness direction of the membrane. The number of divisions can be appropriately selected according to a thickness of the membrane. The number of divisions is at least 5 or more. For example, in a case of a membrane having a thickness of 200 μm, division is performed 20 times from a surface X to be described later. A size of a division width means a width in the thickness direction of the membrane, and does not mean a width in the photograph. In comparison of a pore diameter in the thickness direction of the membrane, the pore diameter is compared as an average pore diameter of each section. An average pore diameter of each section may be, for example, an average value of 50 pores in each section of a membrane cross-sectional view. The membrane cross-sectional view in this case may be obtained, for example, with a width of 80 µm (a distance of 80 µm in a direction parallel to a surface). In this case, with respect to a section in which 50 pores cannot be measured because pores are large, it is sufficient to measure as many as the number that can be taken in the section. In addition, in this case, in a case where a pore is large and does not fit within the section, a size of the pore is measured over the other sections.

The layered compact portion having the smallest pore diameter refers to a layered portion of the porous membrane corresponding to a section where an average pore diameter becomes smallest among sections of the membrane cross section. The compact portion may consist of portions corresponding to one section, or may consist of portions corresponding to a plurality of sections such as 2 or 3 sections, which have an average pore diameter within 1.1 times that of a section where an average pore diameter is minimum. It is sufficient for a thickness of the compact portion to be 0.5 µm to 50 µm, and it is preferably 0.5 µm to 30 µm. In the present specification, an average pore diameter of the compact portion is denoted as the minimum pore diameter of the porous membrane. The minimum pore diameter of the porous membrane is preferably 0.02 µm to 1.5 µm, and is more preferably 0.02 µm to 1.3 µm. The reason for this is because such a minimum pore diameter of the porous membrane can prevent permeation of at least normal cells. Here, an average pore diameter of the compact portion is measured by ASTM F316-80.

The porous membrane has the compact portion within an inner side thereof. The inner side means that the compact portion is not in contact with the surface of the membrane. The phrase "having the compact portion within the inner side thereof" means that the compact portion is not the closest section to any surface of the membrane. In the immunoisolation membrane, by using the porous membrane having a structure having the compact portion within the inner side thereof, permeability of a substance intended to permeate therethrough is unlikely to be diminished as compared to a case of using a porous membrane having the same compact portion in contact with the surface thereof. Although not bound by any theory, it is perceived that protein adsorption is less likely to occur due to the presence of the compact portion within the inner side.

It is preferable that the compact portion be biased to one of the front surface side than a central portion in thickness of the porous membrane. Specifically, the compact portion is preferably located between any one surface of the porous membrane and a portion at a distance of two-fifth of the porous membrane from the surface, is more preferably located between any one surface of the porous membrane and a portion at a distance of one-third of the porous membrane from the surface, and is even more preferably located between any one surface of the porous membrane and a portion at a distance of one-fourth of the porous membrane from the surface. This distance may be determined from the photograph of the membrane cross section described above. In the present specification, the surface of the porous membrane closer to the compact portion is referred to as a "surface X".

In the porous membrane, a pore diameter continuously increases in the thickness direction from the compact portion toward at least one of the surfaces. In the porous membrane, the pore diameter may continuously increase in the thickness direction toward the surface X from the compact portion, the pore diameter may continuously increase in the thickness direction toward the surface opposite to the surface X from the compact portion, and the pore diameter may continuously increase in the thickness direction toward any surface of the porous membrane from the compact portion. Among them, it is preferable that the pore diameter continuously increase in the thickness direction toward at least the surface opposite to the surface X from the compact portion, and it is preferable that the pore diameter continuously increase in the thickness direction toward any surface of the porous membrane from the compact portion. The sentence "the pore diameter continuously increases in the thickness direction" means that a difference in average pore diameters between sections adjacent to each other in the thickness direction increases by 50% or less of a difference between maximum average pore diameters (maximum pore diameter) and minimum average pore diameters (minimum pore diameter), preferably increases by 40% or less, and more preferably increases by 30% or less. The phrase "continuously increasing" essentially means that a pore diameter increases uniformly without decreasing, but a decreasing portion may occur accidentally. For example, in a case of combining two sections from the surface, in a case where an average value of a combination increases uniformly (uniformly decreases toward the compact portion from the surface), it can be determined that "the pore diameter continuously increases in the thickness direction toward the surface of the membrane from the compact portion".

A structure of the porous membrane in which a pore diameter continuously increases in the thickness direction can be realized by, for example, a manufacturing method to be described later.

A maximum pore diameter of the porous membrane is preferably more than 1.5 µm and 25 µm or less, is more preferably 1.8 µm to 23 µm, and is even more preferably 2.0 µm to 21 µm. In the present specification, an average pore diameter of a section having the maximum average pore diameter among section of the membrane cross section is referred to as the "maximum pore diameter of the porous membrane".

A ratio of the maximum pore diameter of the porous membrane to an average pore diameter of the compact portion (a ratio of a maximum pore diameter to a minimum pore diameter of the porous membrane, which is a value obtained by dividing the maximum pore diameter by the minimum pore diameter, an "anisotropy ratio" in the present specification) is preferably 3 or more, is more preferably 4 or more, and is even more preferably 5 or more. The reason is that an average pore diameter except for that of the compact portion increases to increase substance permeability of the porous membrane. In addition, the anisotropy ratio is preferably 25 or less and is more preferably 20 or less. A ratio of the maximum pore diameter to the minimum pore diameter of the porous membrane can be set to 3.0 to 20.0, for example.

It is preferable that a section line with a maximum average pore diameter be a section closest to any surface of the membrane or a section in contact with that section.

In the section closest to any surface of the membrane, it is preferable that an average pore diameter be more than 0.05 µm and 25 µm or less, be more preferably more than 0.08 µm and 23 µm or less, and be even more preferably more than 0.5 µm and 21 µm or less. In addition, a ratio of an average pore diameter of the compact portion to an average pore diameter of the section closest to any surface of the membrane is preferably 1.2 to 20, is more preferably 1.5 to 15, and is even more preferably 2 to 13.

(Elemental Distribution of Porous Membrane)

Formulas (I) and (II) are preferably satisfied for at least one surface of the porous membrane.

$$B/A \leq 0.7 \quad (I)$$

$$A \geq 0.015 \quad (II)$$

In the formula, A represents a ratio of an N element (nitrogen atom) to a C element (carbon atom) on a surface of the membrane, and B represents a ratio of the N element to the C element at a depth of 30 nm from the same surface.

Formula (II) shows that a certain amount or more of N element is present on at least one surface of the porous membrane, and Formula (I) shows that an N element in the porous membrane is localized at a depth of less than 30 nm of the surface. The N element is preferably derived from a nitrogen-containing polymer. In addition, the nitrogen-containing polymer is preferably polyvinyl pyrrolidone.

With the surface satisfying Formulas (I) and (II), a bioaffinity of the porous membrane, particularly, a bioaffinity of the surface side satisfying Formulas (I) and (II) becomes high.

In the porous membrane, either one of surfaces may satisfy Formulas (I) and (II), or both surfaces may satisfy Formulas (I) and (II), but it is preferable that both surfaces satisfy Formulas (I) and (II). In a case where either one of surfaces satisfies Formulas (I) and (II), the surface thereof may be in an inside or an outside of a chamber for transplantation to be described later, but the surface is preferably in the inside thereof. In addition, in a case where only one of any surface satisfies Formulas (I) and (II), a surface satisfying Formulas (I) and (II) is preferably the surface X.

In the present specification, a ratio (A value) of N element to C element on the membrane surface and a ratio (B value) of N element to C element at a depth of 30 nm from the surface are obtained by calculating using XPS measurement results. The XPS measurement is X-ray photoelectron spectroscopy, which is a method for irradiating a membrane surface with X-rays, measuring kinetic energy of photoelectrons emitted from the membrane surface, and analyzing a composition of elements constituting the membrane surface. Under conditions using a monochromated Al-Kα ray described in Examples, the A value is calculated from results at the start of sputtering, and the B value is calculated from time results, which are calculated that the ray is at 30 nm from the surface of the membrane measured from a sputtering rate.

It is sufficient for B/A to be 0.02 or more, and it is preferably 0.03 or more, and is more preferably 0.05 or more.

A is preferably 0.050 or more and is more preferably 0.080 or more. In addition, it is sufficient for A to be 0.20 or less, and it is preferably 0.15 or less, and is more preferably 0.10 or less.

It is sufficient for B to be 0.001 to 0.10, and it is preferably 0.002 to 0.08, and is more preferably 0.003 to 0.07.

In a method for manufacturing the porous membrane which will be described later, the elemental distribution of the porous membrane, especially the distribution of an N element, can be controlled by a moisture concentration contained in the temperature-controlled humid air, a time to apply the temperature-controlled humid air, a temperature of a coagulation liquid, an immersion time, a temperature of a diethylene glycol bath for washing, an immersion time in the diethylene glycol bath for washing, a speed of a porous manufacture line, and the like. The distribution of the N element can also be controlled by an amount of moisture contained in a stock solution for forming a membrane.

(Composition of Porous Membrane)

The porous membrane contains a polymer. It is preferable that the porous membrane be essentially composed of a polymer.

The polymer forming the porous membrane is preferably biocompatible. The term "biocompatible" means that the polymer has non-toxic and non-allergenic properties, but does not have properties such that the polymer is encapsulated in a living body.

The number average molecular weight (Mn) of the polymer is preferably 1,000 to 10,000,000 and is more preferably 5,000 to 1,000,000.

Examples of polymers include thermoplastic or thermosetting polymers. Specific examples of polymers include polysulfone, cellulose acylate, nitrocellulose, sulfonated polysulfone, polyethersulfone, polyacrylonitrile, styrene-acrylonitrile copolymer, styrene-butadiene copolymer, saponified ethylene-vinyl acetate copolymer, polyvinyl alcohol, polycarbonate, an organosiloxane-polycarbonate copolymer, a polyester carbonate, an organopolysiloxane, a polyphenylene oxide, a polyamide, a polyimide, polyamideimide, polybenzimidazole, ethylene vinyl alcohol copolymer, polytetrafluoroethylene (PTFE), and the like. From the viewpoints of solubility, optical physical properties, electrical physical properties, strength, elasticity, and the like, polymers may be homopolymers, copolymers, polymer blends, or polymer alloys.

Among these, polysulfone and cellulose acylate are preferable, and polysulfone is more preferable.

The porous membrane may contain other components other than polymers as additives.

Examples of additives include common salts, metal salts of inorganic acids such as lithium chloride, sodium nitrate, potassium nitrate, sodium sulfate, and zinc chloride; metal salts of organic acids such as sodium acetate and sodium formate; polyethylene glycol; polymers such as polyvinylpyrrolidone; polymer electrolytes such as sodium polystyrene sulfonate and polyvinyl benzyl trimethyl ammonium chloride; ionic surfactants such as sodium dioctyl sulfosuccinate and sodium alkyl sodium taurate; and the like. The additive may act as a swelling agent for a porous structure.

The porous membrane is preferably a membrane formed from a single composition as a single layer, and preferably not has a laminated structure of a plurality of layers.

(Method for Manufacturing Porous Membrane)

A method for manufacturing the porous membrane is not particularly limited as long as the method can form the porous membrane having the above-mentioned structure, and any general methods for forming a polymer membrane can be used. Examples of methods for forming a polymer membrane include a stretching method, a casting method, and the like.

For example, in the casting method, it is possible to produce a porous membrane having the above-mentioned structure by adjusting the type and amount of a solvent used in a stock solution for forming a membrane, and a drying method after casting.

Manufacture of a porous membrane by a casting method can be carried out by a method including, for example, the following (1) to (4) in this order.

(1) A stock solution for forming a membrane, which contains a polymer, if necessary an additive and, if necessary a solvent, is flow-cast on a support while being in a dissolved state.

(2) The surface of the flow-cast liquid membrane is exposed to temperature-controlled humid air.

(3) The membrane obtained after being exposed to temperature-controlled humid air is immersed in a coagulation liquid.

(4) A support is peeled off if necessary.

A temperature of temperature-controlled humid air may be 4° C. to 60° C. and is preferably 10° C. to 40° C. A relative humidity of the temperature-controlled humid air may be 30% to 70% and is preferably 40% to 50%. An absolute humidity of the temperature-controlled humid air is preferably 1.2 to 605 g/kg air, and is more preferably 2.4 to 300 g/kg air. The temperature-controlled humid air may be applied at a wind speed of 0.1 μm/s to 10 μm/s for 0.1 seconds to 30 seconds, preferably 1 second to 10 seconds.

In addition, an average pore diameter and position of the compact portion can also be controlled by a moisture concentration contained in the temperature-controlled humid air and a time of applying the temperature-controlled humid air. An average pore diameter of the compact portion can also be controlled by an amount of moisture contained in a stock solution for forming a membrane.

By applying the temperature-controlled humid air to the surface of the liquid membrane as described above, it is possible to cause coacervation from the surface of the liquid membrane toward the inside of the liquid membrane by controlling evaporation of a solvent. By immersing the membrane in a coagulation liquid containing a solvent having low solubility of the polymer but compatible with the solvent of the polymer in this state, the above-mentioned coacervation phase is fixed as fine pores, and pores other than the fine pores can also be formed.

A temperature of the coagulation liquid may be −10° C. to 80° C. in a process of immersing the membrane in the coagulation liquid. By changing a temperature during this period, it is possible to control a size of a pore diameter up to a support surface side by adjusting a time from the formation of the coacervation phase on the support surface side to the solidification from the compact portion. In a case where a temperature of the coagulation liquid is raised, the formation of the coacervation phase becomes faster and a time for solidification becomes longer, and therefore the pore diameter toward the support surface side tends to become large. On the other hand, in a case where a temperature of the coagulation liquid is lowered, the formation of the coacervation phase becomes slower and a time for solidification becomes shorter, and therefore the pore diameter toward the support surface side is unlikely to become large.

As the support, a plastic film or a glass plate may be used. Examples of materials of the plastic film include polyester such as polyethylene terephthalate (PET), polycarbonate, acrylic resin, epoxy resin, polyurethane, polyamide, polyolefin, a cellulose derivative, silicone, and the like. As the support, a glass plate or PET is preferable, and PET is more preferable.

The stock solution for forming a membrane may contain a solvent. A solvent having high solubility of the polymer to be used (hereinafter referred to as "favorable solvent") may be used depending on a polymer to be used. As a favorable solvent, it is preferable that the solvent be quickly substituted with the coagulation liquid in a case where the membrane is immersed in the coagulation liquid. Examples of solvents include N-methyl-2-pyrrolidone, dioxane, tetrahydrofuran, dimethylformamide, dimethylacetamide, or a mixed solvent thereof in a case where the polymer is polysulfone and the like; dioxane, N-methyl-2-pyrrolidone, dimethylformamide, dimethylacetamide, dimethylsulfoxide, or a mixed solvent thereof in a case where the polymer is polyacrylonitrile and the like; dimethylformamide, dimethylacetamide, or a mixed solvent thereof in a case where the polymer is polyamide and the like; acetone, dioxane, tetrahydrofuran, N-methyl-2-pyrrolidone, or a mixed solvent thereof in a case where the polymer is cellulose acetate and the like.

In addition to a favorable solvent, the stock solution for forming a membrane preferably use a solvent (hereinafter referred to as "non-solvent") in which the solubility of the polymer is low but is compatible with the solvent of the polymer. Examples of non-solvents include water, cellosolves, methanol, ethanol, propanol, acetone, tetrahydrofuran, polyethylene glycol, glycerin, and the like. Among these, it is preferable to use water.

A concentration of the polymer as the stock solution for forming a membrane may be 5% by mass to 35% by mass, is preferably 10% by mass to 30% by mass. By setting the concentration thereof to 35 mass % or less, sufficient permeability (for example, water permeability) can be imparted to the obtained porous membrane. By setting the concentration thereof to 5 mass % or more, the formation of a porous membrane which selectively allows substances to permeate can be secured. An amount of additive to be added is not particularly limited as long as the homogeneity of the stock solution for forming a membrane is not lost by the addition, but is 0.5 mass % to 10 mass % respect to a general solvent. In a case where the stock solution for forming a membrane contains a non-solvent and a favorable solvent, a ratio of the non-solvent to the favorable solvent is not particularly limited as long as a mixed solution can be maintained in a homogeneous state, but is preferably 1.0% by mass to 50% by mass, is more preferably 2.0% by mass to 30% by mass, and is even more preferably 3.0% by mass to 10% by mass.

As the coagulation liquid, it is preferable to use a solvent having a low solubility of the polymer used. Examples of such solvents include water, alcohols such as methanol, ethanol, and butanol; glycols such as ethylene glycol and diethylene glycol; aliphatic hydrocarbons such as ether, n-hexane, and n-heptane; glycerol such as glycerin; and the like. Examples of preferred coagulation liquids include water, alcohols, or a mixture of two or more of these. Among these, it is preferable to use water.

After immersion in the coagulation liquid, it is also preferable to perform washing with a solvent different from the coagulation liquid that has been used. Washing can be carried out by immersing in a solvent. Diethylene glycol is preferable as a washing solvent. Distribution of an N element in the porous membrane can be adjusted by adjusting either or both of a temperature and an immersion time of diethylene glycol in which a film is immersed by using diethylene glycol as a washing solvent. In particular, in a case where polyvinylpyrrolidone is used as the stock solution for forming a membrane of the porous membrane, a residual amount of polyvinylpyrrolidone on the membrane can be controlled. After washing with diethylene glycol, furthermore, the membrane may be washed with water.

As the stock solution for forming a membrane for the porous membrane, a stock solution for forming a membrane which is obtained by dissolving polysulfone and polyvinylpyrrolidone in N-methyl-2-pyrrolidone, and adding water is preferable.

Regarding a method for manufacturing the porous membrane, reference can be made to JP1992-349927A (JP-H04-

349927A), JP1992-068966B (JP-H04-068966B), JP1992-351645A (JP-H04-351645A), JP2010-235808A, and the like.

[Other Layers]

The immunoisolation membrane may contain layers other than the porous membrane. Examples of other layers include a hydrogel membrane. As a hydrogel membrane, a biocompatible hydrogel membrane is preferable. Examples thereof include an alginic acid gel membrane, an agarose gel membrane, a polyisopropyl acrylamide membrane, a membrane containing cellulose, a membrane containing a cellulose derivative (for example, methyl cellulose), a polyvinyl alcohol membrane, or the like. The hydrogel membrane is preferably an alginic acid gel membrane. Specific examples of alginic acid gel membranes include a polyion complex membrane of alginic acid-poly-L-lysine-alginic acid.

<Method for Manufacturing Angiogenic Agent>

The angiogenic agent of the embodiment of the present invention can be manufactured by a method including a step of enclosing mesenchymal stem cells with the immunoisolation membrane.

In the present invention, the immunoisolation membrane is used as a constituent member of a chamber for transplantation which is for enclosing mesenchymal stem cells. The chamber for transplantation is used as a container for enclosing mesenchymal stem cells in a case of transplanting the mesenchymal stem cells to a recipient. The immunoisolation membrane can be disposed on at least a part of the surface forming an inner side and an outer side of the chamber for transplantation. By disposing in such a manner, it is possible to protect mesenchymal stem cells enclosed in the chamber for transplantation from immune cells and the like present outside and to introduce nutrients such as water, oxygen, and glucose into the inside of the chamber for transplantation from the outside.

The immunoisolation membrane may be disposed on the entire surface of the surface forming the inner side and the outer side of the chamber for transplantation, and may be disposed a part of the surface corresponding to an area of, for example, 1% to 99%, 5% to 90%, 10% to 80%, 20% to 70% %, 30% to 60%, 40% to 50%, or the like with respect to the entire area. A surface on which the immunoisolation membrane is disposed may be one continuous portion or may be divided into two or more portions.

A shape of the chamber for transplantation is not limited, and may be a shape such as a pouched-like shape, a bag shape, a tube shape, a microcapsule shape, or a drum shape. For example, a drum-shaped chamber for transplantation can be formed by adhering the immunoisolation membrane to the top and bottom of a silicone ring. A shape of the chamber for transplantation is preferably a shape capable of preventing movement within a recipient in a case where the chamber for transplantation is used as an angiogenic agent. Specific examples of shapes of the chamber for transplantation include a cylindrical shape, a disk-like shape, a rectangular shape, an egg shape, a star shape, a circular shape, and the like. The chamber for transplantation may be in a form of a sheet, a strand, a spiral, or the like. The chamber for transplantation may be a chamber for transplantation which encloses the cells or cell structure and becomes the above-described shape only in a case where the chamber for transplantation used as an angiogenic agent.

The chamber for transplantation may contain a biocompatible plastic or the like for maintaining the shape and strength as a container. For example, the surface forming the inner side and the outer side of the chamber for transplantation may be made of an immunoisolation membrane and a biocompatible plastic that does not correspond to the immunoisolation membrane. In addition, in the chamber for transplantation in which the immunoisolation membrane is disposed on the entire surface of the surface forming the inner side and the outer side, a biocompatible plastic having a net-like structure may be further disposed on the outside of the surface forming the inner side and the outer side, from the viewpoint of strength.

It is preferable in the chamber for transplantation that the surface X of the porous membrane be on the inside thereof. That is, it is preferable that the immunoisolation membrane be disposed so that the compact portion of the porous membrane in the immunoisolation membrane is closer to the inside of the chamber for transplantation. By setting the surface X in the inside of the chamber for transplantation, it is possible to make permeability of physiologically active substances higher.

<Angiogenic Agent>

The angiogenic agent of the embodiment of the present invention includes mesenchymal stem cells and the immunoisolation membrane. In the angiogenic agent, mesenchymal stem cells are enclosed in the immunoisolation membrane.

In the angiogenic agent, the immunoisolation membrane may enclose only mesenchymal stem cells (or a cell structure of mesenchymal stem cells), or may enclose, in addition to the mesenchymal stem cells (or the cell structure of mesenchymal stem cells), constituents or components other than the cell structure. For example, mesenchymal stem cells (or a cell structure of mesenchymal stem cells) may be enclosed in the immunoisolation membrane together with a hydrogel, and preferably in a state of being enclosed in the hydrogel. The angiogenic agent may contain pH buffers, inorganic salts, organic solvents, proteins such as albumin, or peptides.

The angiogenic agent may contain only one kind of mesenchymal stem cell (or a cell structure of mesenchymal stem cells) or may contain two or more kinds thereof.

The angiogenic agent may be, for example, a device to be intraperitoneally or subcutaneously transplanted to a recipient. In the present specification, a recipient means a living body to which transplantation is performed. A recipient is preferably a mammal and is more preferably a human.

With respect to the number of transplantation of the angiogenic agent of the embodiment of the present invention, the transplantation may be performed once or the transplantation may be performed twice or more, as necessary.

<Various Use Applications>

According to the present invention, there is provided an angiogenesis method including a step of transplanting, to a subject in need of angiogenesis, a cell transplant device including a mesenchymal stem cell (A) and an immunoisolation membrane (B) that encloses the mesenchymal stem cell.

According to the present invention, there is provided a cell transplant device which is used for angiogenesis procedure, the device including a mesenchymal stem cell (A); and an immunoisolation membrane (B) that encloses the mesenchymal stem cell.

According to the present invention, there is provided use of a cell transplant device to manufacture an angiogenic agent, in which the cell transplant device includes a mesenchymal stem cell (A); and an immunoisolation membrane (B) that encloses the mesenchymal stem cell.

In the various use applications described above, a preferable aspect is the same as described above.

The present invention will be more specifically described using the following examples, but is not limited by the examples.

EXAMPLES

[Reference Example 1] Recombinant Peptide (Recombinant Gelatin)

The following CBE3 (which is disclosed in WO2008/103041A) was prepared as a recombinant peptide (recombinant gelatin).
CBE3:
Molecular weight: 51.6 kDa
Structure: GAP[(GXY)$_{63}$]$_3$G (SEQ ID NO: 11)
Number of amino acids: 571
Number of RGD sequences: 12
Imino acid content: 33%
Almost 100% of amino acids have a repeating structure of GXY In the amino acid sequence of CBE3, serine, threonine, asparagine, tyrosine, and cysteine are not included. CBE3 has an ERGD sequence (SEQ ID NO: 10).
Isoelectric point: 9.34
GRAVY value: −0.682
1/IOB value: 0.323
Amino acid sequence (SEQ ID NO: 1 in a sequence listing) (which is the same as that of SEQ ID NO: 3 in WO2008/103041A. However, X at the end is corrected to "P")

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)$_3$G

[Reference Example 2] Production of Porous Body of Recombinant Peptide

[PTFE-Thickness.Cylindrical Container]

A cylindrical cup-shaped polytetrafluoroethylene (PTFE) container with a bottom-surface thickness of 3 mm, a diameter of 51 mm, a side-surface thickness of 8 mm, and a height of 25 mm was prepared. In a case where the cylindrical cup has a curved surface as a side surface, the side surface is closed by PTFE with 8 mm and a bottom surface (circular shape of a flat plate) is also closed by PTFE with 3 mm. In contrast, an upper surface is in an open shape. Accordingly, an inner diameter of the cylindrical cup is 43 mm. Hereinafter, this container is referred to as a PTFE-thickness.cylindrical container.

[Aluminum Glass Plate-Cylindrical Container]

A cylindrical cup-shaped aluminum container with a thickness of 1 mm and a diameter of 47 mm was prepared. In a case where the cylindrical cup has a curved surface as a side surface, the side surface is closed by aluminum with 1 mm and a bottom surface (circular shape of a flat plate) is also closed by aluminum with 1 mm. In contrast, an upper surface is in an open shape. In addition, TEFLON (registered trademark) with a thickness of 1 mm is evenly spread only in the inside of the side surface, and as a result, an inner diameter of the cylindrical cup is 45 mm. In addition, in the bottom surface of this container, a glass plate with 2.2 mm is bonded on the outside of aluminum. Hereinafter, this container is referred to as an aluminum glass plate cylindrical container.

[Freezing Step in which Difference in Temperature is Small, and Drying Step]

A CBE3 aqueous solution was poured into the PTFE-thickness.cylindrical container or the aluminum glass plate-cylindrical container, and was cooled down from the bottom surface using a cooling shelf within a vacuum freeze dryer (TF5-85ATNNN: Takara Co., Ltd.). Combinations of setting of the container, a final concentration of the CBE3 aqueous solution, an amount of the solution, and a temperature of the shelf at this time were prepared as described below.

Condition A:

PTFE-thickness.cylindrical container, final concentration of CBE3 aqueous solution of 4 mass %, and amount of aqueous solution of 4 mL. As the setting for the temperature of the shelf, the temperature was cooled down until the temperature reached −10° C., and freezing was performed for 1 hour at −10° C., for 2 hours at −20° C., for 3 hours at −40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased (1.9×10$^5$ Pa). Then, the product was taken out of the vacuum freeze dryer. Therefore, a porous body was obtained.

Condition B:

Aluminum-glass plate-cylindrical container, final concentration of CBE3 aqueous solution of 4 mass %, and amount of aqueous solution of 4 mL.

As the setting for the temperature of the shelf, the temperature was cooled down until the temperature reached −10° C., and freezing was performed for 1 hour at −10° C., for 2 hours at −20° C., for 3 hours at −40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased (1.9×10$^5$ Pa). Then, the product was taken out of the vacuum freeze dryer. Therefore, a porous body was obtained.

Condition C:

PTFE-thickness.cylindrical container, final concentration of CBE3 aqueous solution of 4 mass %, and amount of aqueous solution of 10 mL. As the setting for the temperature of the shelf, the temperature was cooled down until the temperature reached −10° C., and freezing was performed for 1 hour at −10° C., for 2 hours at −20° C., for 3 hours at −40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased (1.9×10$^5$ Pa). Then, the product was taken out of the vacuum freeze dryer. Therefore, a porous body was obtained.

[Measurement of Temperature in Each Freezing Step]

Regarding each of Conditions A to C, a liquid temperature of a surface of water in a circular center portion within a container was measured as a liquid temperature (non-cooled surface liquid temperature) of the farthest portion from a cooling side in a solution, and a liquid temperature of a bottom portion within the container was measured as a liquid temperature (cooled surface liquid temperature) of the closest portion to the cooling side in the solution.

As a result, each temperature and a profile of the difference in temperature are as shown in FIGS. 1 to 3.

It can be seen from FIGS. 1 to 3 that in Conditions A to C, the liquid temperature fell below 0° C., which was a melting point, in a setting section of a temperature of a shelf of −10° C. (before the temperature was decreased to −20° C.), and the solution was in a (unfrozen and overcooled) state where freezing did not occur in that state. In addition, in this state, the difference in temperature between the cooled surface liquid temperature and the non-cooled surface liquid temperature was lower than or equal to 2.5° C. In the present specification, the "difference in temperature" means "non-cooled surface liquid temperature"–"cooled surface liquid temperature". Then, the timing at which the liquid temperature rapidly rose to around 0° C. by further decreasing the temperature of the shelf to −20° C. was confirmed, and it can be seen that freezing started due to generation of solidification heat at the timing. In addition, it was also possible to confirm that ice formation actually started at this timing. Thereafter, the temperature was around 0° C. while the certain time passed. At this time, the product was in a state where a mixture of water and ice was present. The temperature finally started to be decreased again from 0° C., and at this time, liquid disappeared and was changed to ice. Accordingly, the measured temperature was the solid temperature within the ice, that is, was not the liquid temperature.

Hereinafter, regarding Conditions A to C, the difference in temperature in a case where the non-cooled surface liquid temperature reached a melting point (0° C.), the difference in temperature immediately before the temperature of the shelf was decreased from −10° C. to −20° C., and the difference in temperature immediately before the generation of solidification heat are described. The "difference in temperature immediately before" referred to in the present invention indicates the highest temperature within the difference in temperature which can be detected between 1 second to 20 seconds before an event (such as the generation of solidification heat).

Condition A

Difference in temperature in a case where a non-cooled surface liquid temperature reached a melting point (0° C.): 1.1° C.

Difference in temperature immediately before a temperature was decreased from −10° C. to −20° C.: 0.2° C.

Difference in temperature immediately before generation of solidification heat: 1.1° C.

Condition B

Difference in temperature in a case where a non-cooled surface liquid temperature reached a melting point (0° C.): 1.0° C.

Difference in temperature immediately before a temperature was decreased from −10° C. to −20° C.: 0.1° C.

Difference in temperature immediately before generation of solidification heat: 0.9° C.

Condition C

Difference in temperature in a case where a non-cooled surface liquid temperature reached a melting point (0° C.): 1.8° C.

Difference in temperature immediately before a temperature was decreased from −10° C. to −20° C.: 1.1° C.

Difference in temperature immediately before generation of solidification heat: 2.1° C.

[Reference Example 3] Production of Biocompatible Polymer Block (Pulverization and Cross-Linking of Porous Body)

The CBE3 porous bodies of Conditions A and B which were obtained in Reference Example 2 were pulverized by NEW POWER MILL (Osaka Chemical Co., Ltd., NEW POWER MILL PM-2005). The pulverization was performed by one minute×5 times, that is, for 5 minutes in total at the maximum rotation speed. The obtained pulverized substances were sized with a stainless steel sieve to obtain uncross-linked blocks with 25 to 53 µm, 53 to 106 µm, and 106 to 180 µm. Then, the uncross-linked blocks were subjected to thermal cross-linking (cross-linking was performed for times of six kinds of 8 hours, 16 hours, 24 hours, 48 hours, 72 hours, and 96 hours) at 160° C. under reduced pressure to obtained biocompatible polymer blocks (CBE3 blocks).

Hereinafter, a porous body-derived block of Condition A which is cross-linked for 48 hours is referred to as E, and a porous body-derived block of Condition B which is cross-linked for 48 hours is referred to as F. E and F are blocks with a small difference in temperature which are formed from porous bodies produced through a freezing step in which the difference in temperature is small. Moreover, since the difference in cross-linking time did not influence the performance in the evaluation of the present examples, hereafter, the blocks cross-linked for 48 hours were used as a representative. There was no difference in the performance between E and F. In Reference Examples, Examples, and Comparative examples below, biocompatible polymer blocks which satisfied Condition A, had sizes of 53 to 106 µm, and were produced with the cross-linking time of 48 hours were used.

[Reference Example 4] Measurement of Tap Density of Biocompatible Polymer Block

The tap density is a value indicating how many blocks can be densely packed in a certain volume, and it can be said that as the value becomes lower, the blocks cannot be densely packed, that is, the structure of the block is complicated. The tap density was measured as follows. First, a funnel with a cap (having a cylindrical shape with a diameter of 6 mm and a length of 21.8 mm: a capacity of 0.616 cm$^3$) attached at the tip thereof was prepared, and a mass of only the cap was measured. Then, the cap was attached to the funnel, and blocks were poured from the funnel so as to be accumulated in the cap. After pouring a sufficient amount of blocks, the cap portion was hit 200 times on a hard object such as a desk, the funnel was removed, and the blocks were leveled off with a spatula. A mass was measured in a state where the cap was filled up with the blocks. The tap density was determined by calculating a mass of only the blocks from the difference between the mass of the cap filled up with the blocks and the mass of only the cap, and dividing the mass of only the blocks by the volume of the cap. As a result, the tap density of the biocompatible polymer block of Reference Example 3 was 98 mg/cm$^3$.

[Reference Example 5] Measurement of Cross-Linking Degree of Biocompatible Polymer Block The cross-linking degree (the number of times of cross-linking per molecule) of the blocks cross-linked in Reference Example 3 was calculated. The measurement was performed by a TNBS (2,4,6-trinitrobenzene sulfonic acid) method.

<Sample Preparation>

A sample (about 10 mg), 4 mass % NaHCO$_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then the mixture was allowed to stand for 16 hours or longer at 37° C. to prepare a sample.

<Preparation of Blank>

A sample (about 10 mg), 4 mass % NaHCO$_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then the mixture was allowed to stand for 16 hours or longer at 37° C. to prepare a blank.

The absorbances (345 nm) of the sample and the blank which were diluted 10 times with pure water were measured, and the cross-linking degree (the number of times of cross-linking per molecule) was calculated from (Expression 2) and (Expression 3).

(As−Ab)/14,600×V/w     (Expression 2)

(Expression 2) represents the amount (molar equivalent) of lysine per 1 g of a recombinant peptide.

(In the expression, As represents a sample absorbance, Ab represents a blank absorbance, V represents an amount (g) of reaction liquid, and w represents a mass (mg) of the recombinant peptide.)

1−(sample (Expression 2)/uncross-linked recombinant peptide (Expression 2))×34     (Expression 3)

(Expression 3) represents the number of times of cross-linking per molecule.

As a result, the cross-linking degree of the biocompatible polymer blocks of Reference Example 3 was 4.2.

[Reference Example 6] Measurement of Water Absorption Rate of Biocompatible Polymer Block The water absorption rate of biocompatible polymer block produced in Reference Example 3 was calculated.

A 3 cm×3 cm bag made of nylon mesh was filled with about 15 mg of the biocompatible polymer block at 25° C., was swollen in ion exchange water for 2 hours, and then was dried with air for 10 minutes. The mass of the bag was measured at each stage, and the water absorption rate was determined according to (Expression 4).

Water absorption rate=(w2−w1−w0)/w0     (Expression 4)

(In the expression, w0 represents a mass of a material before water absorption, w1 represents a mass of an empty bag after water absorption, and w2 represents a mass of the whole bag containing the material after water absorption.)

As a result, the water absorption rate of the block of Reference Example 3 was 786%.

[Reference Example 7] Production of Cell Structure

Mouse adipose-derived mesenchymal stem cells (mADSCs) were suspended in a D-MEM medium (Dulbecco's modified Eagle medium) containing 10% FBS (fetal bovine serum), the biocompatible polymer blocks (53 to 106 μm) produced in Reference Example 3 was added thereto, and finally, the mADSCs (1.2×10$^8$ cells) and the biocompatible polymer blocks (0.25 mg) suspended in 4 mL of the medium were seeded in EZSPHERE (registered trademark) dish Type 903 which is a cell non-adhesive dish of 35 mm (manufactured by AGC TECHNO GLASS CO., Ltd., a spheroid well diameter is 800 μm, a spheroid well depth is 300 μm, the number of spheroid wells is about 1,200, a bottom surface is a culture surface having recessed portions, and a side outer wall portion standing on the periphery of the culture surface is provided). The dish was allowed to stand for 48 hours at 37° C. in a CO$_2$ incubator to obtain about 1,200 uniform cell structures.

[Reference Example 8] Production of Immunoisolation Membrane and Evaluation of Pore Diameter <Production of Porous Membrane>

15 parts by mass of polysulfone (P3500 manufactured by Solvay), 15 parts by mass of polyvinylpyrrolidone (K-30 manufactured by Nippon Shokubai Co., Ltd.), 1 part by mass of lithium chloride, and 2 parts by mass of water were dissolved in 67 parts by mass of N-methyl-2-pyrrolidone. Thereby, a stock solution for forming a membrane was obtained. This stock solution for forming a membrane was cast on the surface of a PET (polyethylene terephthalate) film with a wet film thickness such that a dry thickness became 50 μm. The flow-cast membrane surface was exposed to air adjusted to 30° C. and relative humidity 80% RH, at 2 m/sec for 5 seconds. Immediately thereafter, the exposed membrane surface was immersed in a 65° C. coagulation liquid tank filled with water. The PET film was peeled off, and thereby a porous membrane was obtained. Thereafter, the porous membrane was put into a diethylene glycol bath at 80° C. for 120 seconds, and then was washed with pure water. Thereby, a porous membrane having a dry thickness of 50 μm was obtained. This porous membrane was used as an immunoisolation membrane.

<Evaluation of Bubble Point>

In a pore diameter distribution measurement test using a permporometer (CFE-1200AEX manufactured by SEIKA CORPORATION), a bubble point of a membrane sample completely wetted by GALWICK (manufactured by Porous-Materials, Inc.) was evaluated after increasing an air pressure at 5 cm$^3$/min.

The bubble point of the porous membrane of Reference Example 8 was 0.58 kg/cm$^2$.

<Evaluation of Thickness and Pore Diameter>

A thickness of the porous membrane was measured using a SEM photograph of the cross section of the membrane.

Comparison of pore diameters in a thickness direction of the porous membrane was performed by comparing pore diameters in 19 parting lines in a case where an SEM photograph of the membrane cross section was divided into 20 in the thickness direction of the membrane. 50 or more consecutive pores that intersect or are in contact with the parting line are selected, each of pore diameters is measured, and an average value is calculated as an average pore diameter. As the pore diameter, not a length of a portion where the selected pore intersects the parting line, but a diameter was used, the diameter being obtained by tracing a pore with a digitizer from the SEM photograph of the cross section of the membrane to calculate an area thereof, and calculating the obtained area as an area of a true circle. In this case, for a parting line in which pores are large and therefore only up to 50 pores can be selected, an average pore diameter is assumed to an average pore diameter obtained by measuring 50 pores by broadening the field of view of an SEM photograph for obtaining the membrane cross section. Pore diameters in the thickness direction of the membrane were compared by comparing the obtained average pore diameter for each parting line. In this case, the smallest average pore diameter was defined as an average pore diameter of the compact portion.

A thickness of the compact portion of the porous membrane was calculated from the following formula.

Film thickness×[(number of parting lines that allows pore diameter be within 1.3 times minimum pore diameter)/19]   (Formula)

Figure 4:
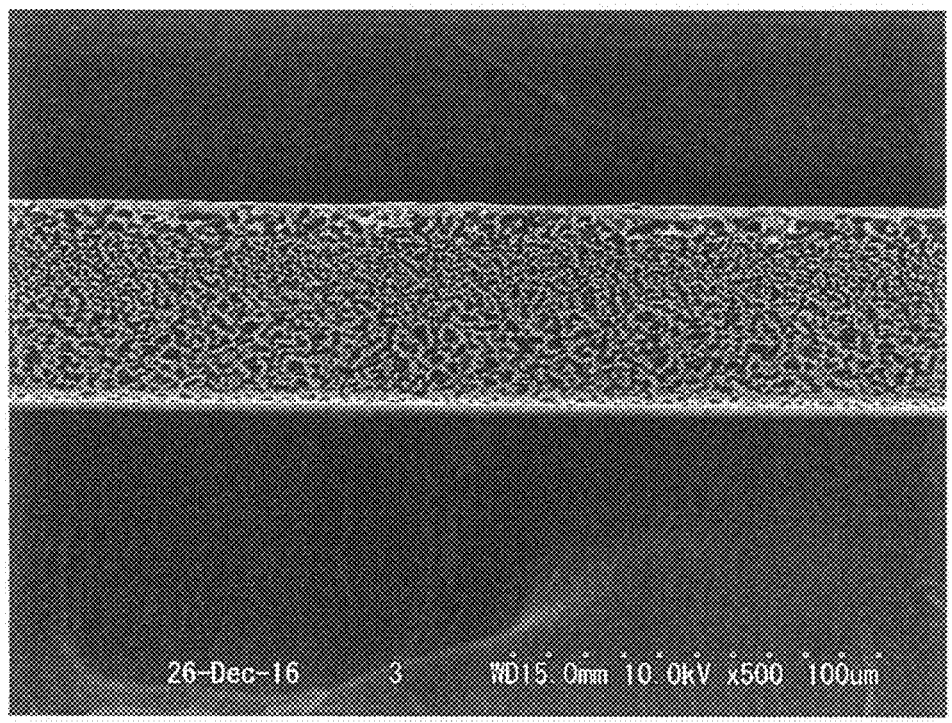
FIG. 4 illustrates a SEM photograph of a cross section of a porous membrane of Reference Example 8.
Figure 5:
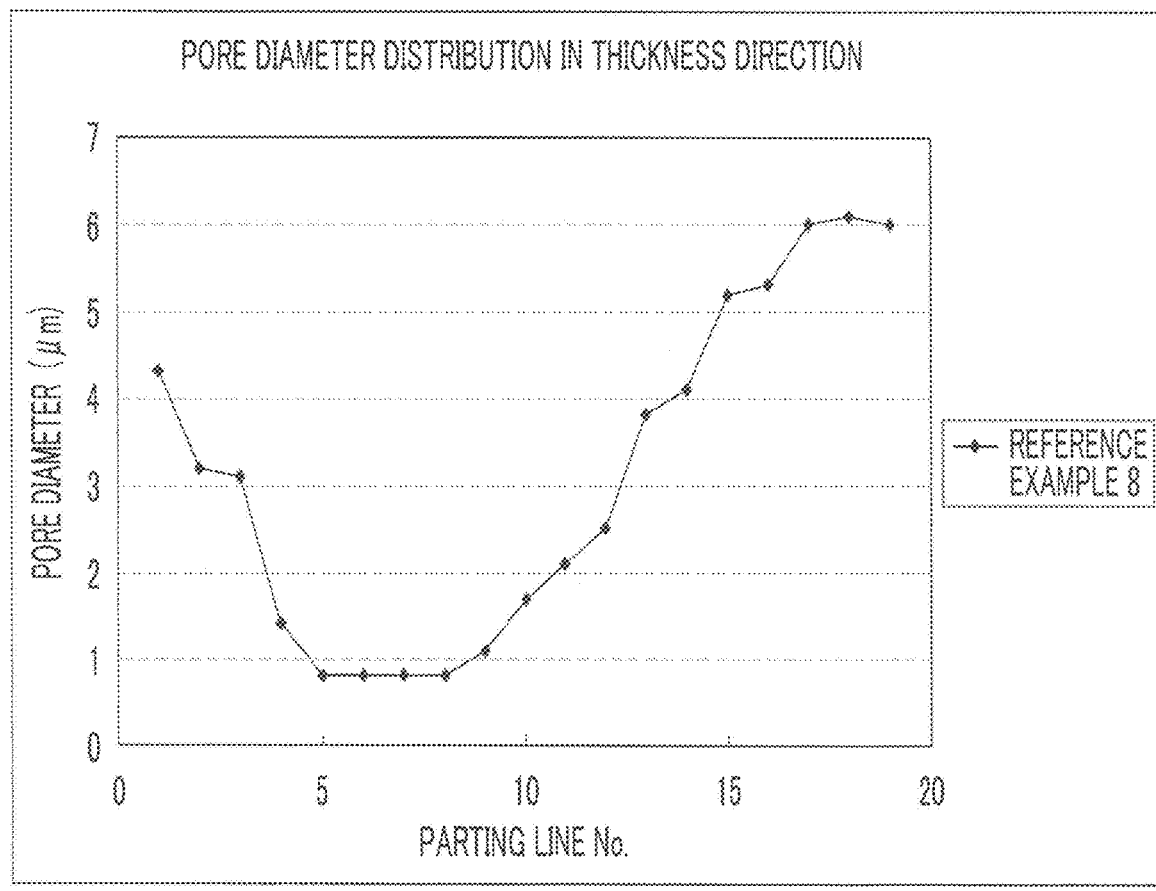
FIG. 5 illustrates a pore diameter distribution in a thickness direction of the porous membrane of Reference Example 8.

FIG. 4 illustrates a SEM photograph of the cross section of the membrane, and FIG. 5 illustrates a pore diameter distribution in the thickness direction. The results of evaluation of the thickness and pore diameter of the porous membrane of Reference Example 8 were as follows.

A thickness of the porous membrane: 55 µm

An average pore diameter of the compact portion (an average value of the minimum pore diameter of the porous membrane): 0.8 µm A ratio of the maximum pore diameter to the minimum pore diameter of the porous membrane: 7.5

A thickness of the compact portion: 10.5 µm

As shown in FIG. 5, in the porous membrane of Reference Example 8, the parting line Nos. 5 to 8 are compact portions, and based on the definition of paragraph number 0097 in the present specification, in the parting line Nos. 1 to 5 and the parting line Nos. 8 to 19, it can be determined that "the pore diameter continuously increases in the thickness direction toward the surface of the membrane from the compact portion".

[Reference Example 9] Production of Cell Transplant Device (Immunoisolation Membrane Only)

The polysulfone porous membrane produced in Reference Example 8 was cut into 3 cm×5 cm. The cut polysulfone porous membrane was folded into two such that a surface to which air was applied during the manufacture became an inner side.

Figure 6:
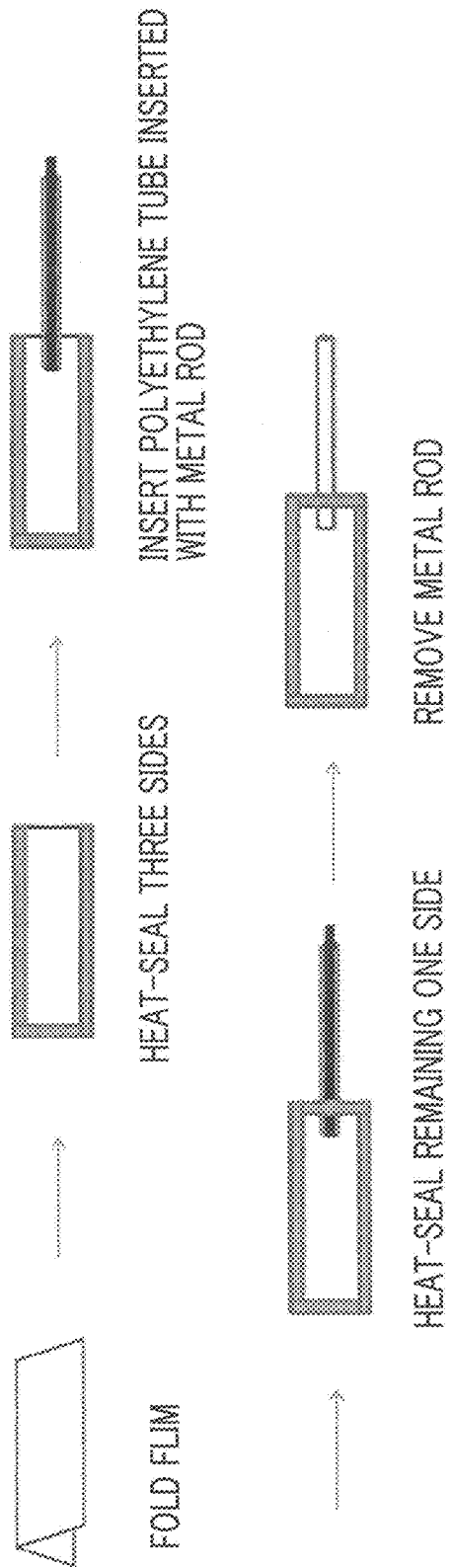
FIG. 6 illustrates a method for producing a cell transplant device (only an immunoisolation membrane).

Thereafter, using a sealer for tea bag (T-230K) manufactured by FUJIIMPULSE CO., LTD., a total of three sides of two long sides and one short side of a 3 cm×2.5 cm rectangle were heated to 260° C. The temperature was measured by a thermocouple. Thereafter, the remaining one side was inserted in a state where a metal rod was inserted into Intramedic polyethylene tube (PE200), and in this state, both were respectively heated at the same temperature using the same sealer. Thereafter, a surrounding portion was cut with a knife so that a width of an end sealing portion became 1 mm. Thereby, a cell transplant device (only an immunoisolation membrane) having a size of 1 cm×2 cm was produced. The production method is shown in FIG. 6.

[Reference Example 10] Production of Immunoisolation Membrane and Evaluation of Pore Diameter 15 parts by mass of polysulfone (P3500 manufactured by Solvay), 15 parts by mass of polyvinylpyrrolidone (K-30 manufactured by Nippon Shokubai Co., Ltd.), 1 part by mass of lithium chloride, and 2 parts by mass of water were dissolved in 67 parts by mass of N-methyl-2-pyrrolidone. Thereby, a stock solution for forming a membrane was obtained. This stock solution for forming a membrane was cast on the surface of a PET film with a wet film thickness such that a dry thickness became 83 µm. The flow-cast membrane surface was exposed to air adjusted to 30° C. and relative humidity 57% RH, at 2 µm/sec for 5 seconds. Immediately thereafter, the exposed membrane surface was immersed in a 70° C. coagulation liquid tank filled with water. The PET film was peeled off, and thereby a porous membrane was obtained. Thereafter, the porous membrane was put into a diethylene glycol bath at 80° C. for 120 seconds, and then was washed with pure water. Thereby, a porous membrane was obtained. This porous membrane was used as an immunoisolation membrane.

The bubble point of the porous membrane of Reference Example 10 was 0.66 kg/cm$^2$.

Figure 8:
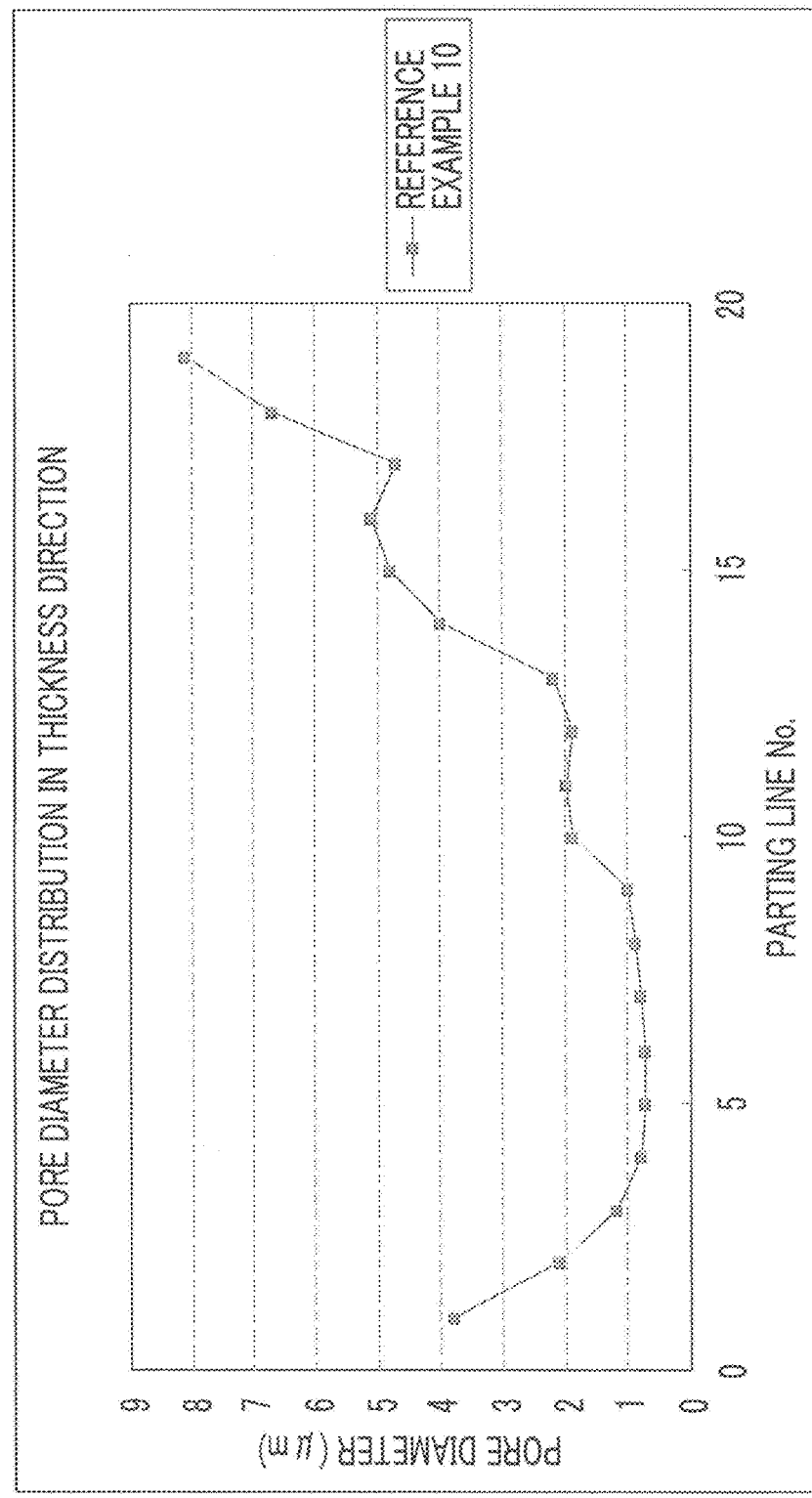
FIG. 8 illustrates a pore diameter distribution in a thickness direction of the porous membrane of Reference Example 10.

A thickness and a pore diameter were evaluated as in the same manner as Reference Example 8. FIG. 7 illustrates a SEM photograph of the cross section of the membrane, and FIG. 8 illustrates a pore diameter distribution in the thickness direction. The results of evaluation of the thickness and pore diameter of the porous membrane of Reference Example 10 were as follows.

A thickness of the porous membrane: 85 µm

An average pore diameter of the compact portion (an average value of the minimum pore diameter of the porous membrane): 0.73 µm A ratio of the maximum pore diameter to the minimum pore diameter of the porous membrane: 11.1

A thickness of the compact portion: 21.8 µm

As shown in FIG. 8, in the porous membrane of Reference Example 10, the parting line Nos. 4 to 8 are compact portions, and based on the definition of paragraph number 0097 in the present specification, in the parting line Nos. 1 to 4 and the parting line Nos. 8 to 19, it can be determined that "the pore diameter continuously increases in the thickness direction toward the surface of the membrane from the compact portion".

[Reference Example 11] Production of Cell Transplant Device

A cell transplant device was produced in the same manner as in Reference Example 9 using the polysulfone porous membrane produced in Reference Example 10 instead of the polysulfone porous membrane produced in Reference Example 8 as the porous membrane.

[Reference Example 12] Production of Immunoisolation Membrane and Evaluation of Pore Diameter 18 parts by mass of polysulfone (P3500 manufactured by Solvay), 12 parts by mass of polyvinylpyrrolidone (K-30), 0.5 parts by mass of lithium chloride, and 1 parts by mass of water were dissolved in 68.5 parts by mass of N-methyl-2-pyrrolidone. Thereby, a stock solution for forming a membrane was obtained. This stock solution for forming a membrane was cast on the surface of a PET film with a wet film thickness such that a dry thickness became 130 µm. The flow-cast membrane surface was exposed to air adjusted to 30° C. and relative humidity 50% RH, at 2 µm/sec for 5 seconds. Immediately thereafter, the exposed membrane surface was immersed in a 50° C. coagulation liquid tank filled with water. The PET film was peeled off, and thereby a porous membrane was obtained. Thereafter, the porous membrane was put into a diethylene glycol bath at 80° C. for 120 seconds, and then was washed with pure water. Thereby, a porous membrane was obtained. This porous membrane was used as an immunoisolation membrane.

The bubble point of the porous membrane of Reference Example 12 was 1.3 kg/cm$^2$.

Figure 9:
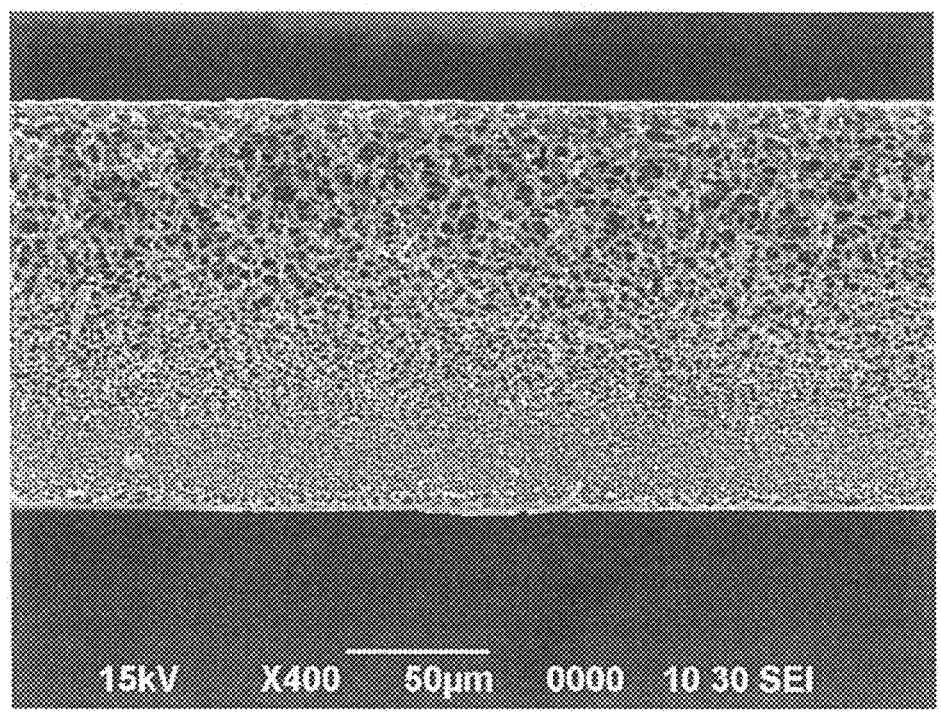
FIG. 9 illustrates a SEM photograph of a cross section of a porous membrane of Reference Example 12.
Figure 10:
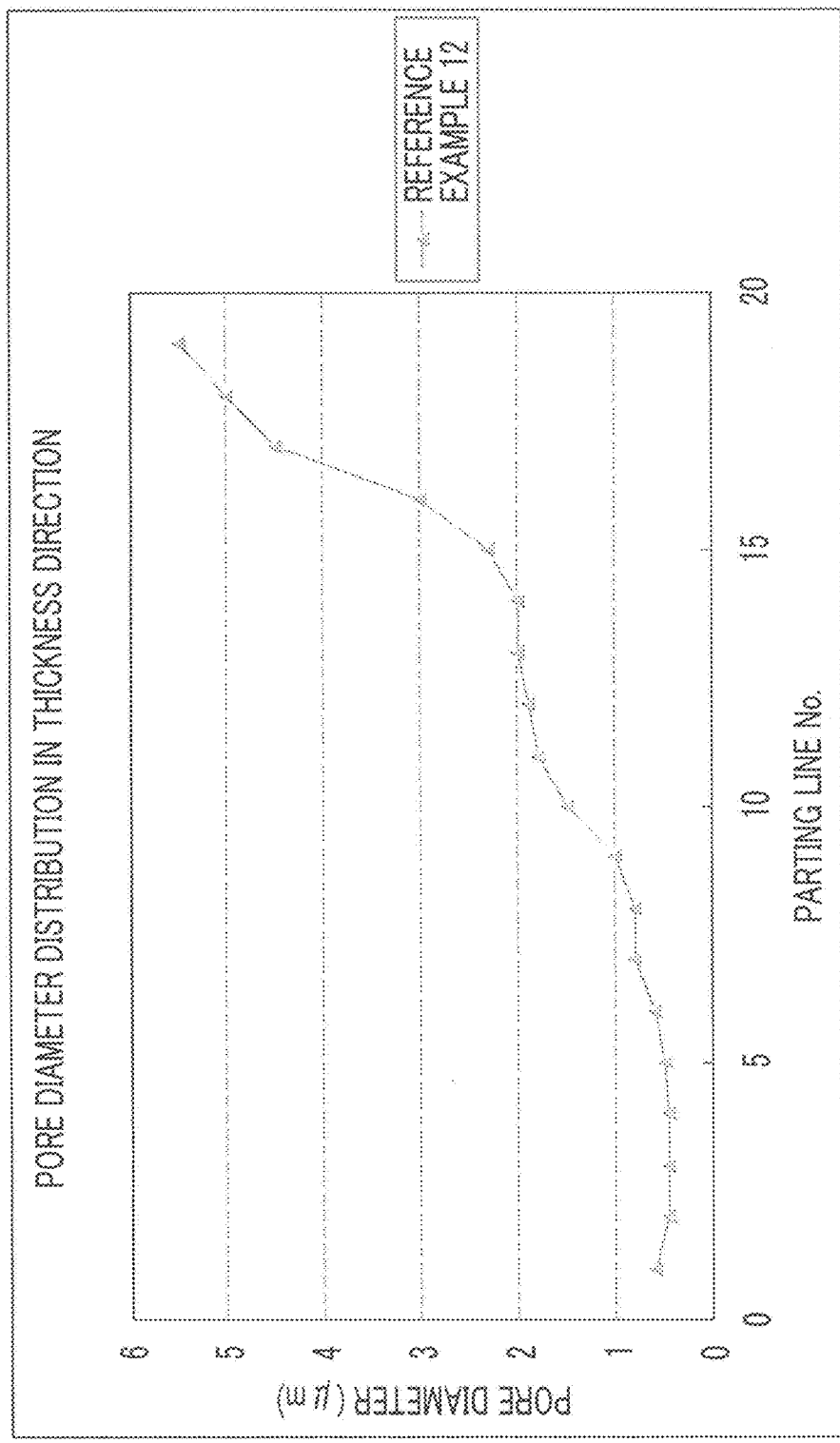
FIG. 10 illustrates a pore diameter distribution in a thickness direction of the porous membrane of Reference Example 12.

A thickness and a pore diameter were evaluated as in the same manner as Reference Example 8. FIG. 9 illustrates a SEM photograph of the cross section of the membrane, and FIG. 10 illustrates a pore diameter distribution in the thickness direction. The results of evaluation of the thickness and pore diameter of the porous membrane of Reference Example 2 were as follows.

A thickness of the porous membrane: 142 μm

An average pore diameter of the compact portion (an average value of the minimum pore diameter of the porous membrane): 0.45 μm A ratio of the maximum pore diameter to the minimum pore diameter of the porous membrane: 12.2

A thickness of the compact portion: 27.4 μm

As shown in FIG. 10, in the porous membrane of Reference Example 12, the parting line Nos. 2 to 5 are compact portions, and based on the definition of paragraph number 0097 in the present specification, in the parting line Nos. 1 and 2 and the parting line Nos. 5 to 19, it can be determined that "the pore diameter continuously increases in the thickness direction toward the surface of the membrane from the compact portion".

[Reference Example 13] Production of Cell Transplant Device (Immunoisolation Membrane Only)

A cell transplant device (immunoisolation membrane only) was produced in the same manner as in Reference Example 9 using the polysulfone porous membrane produced in Reference Example 12 instead of the polysulfone porous membrane produced in Reference Example 8 as the porous membrane.

Figure 11:
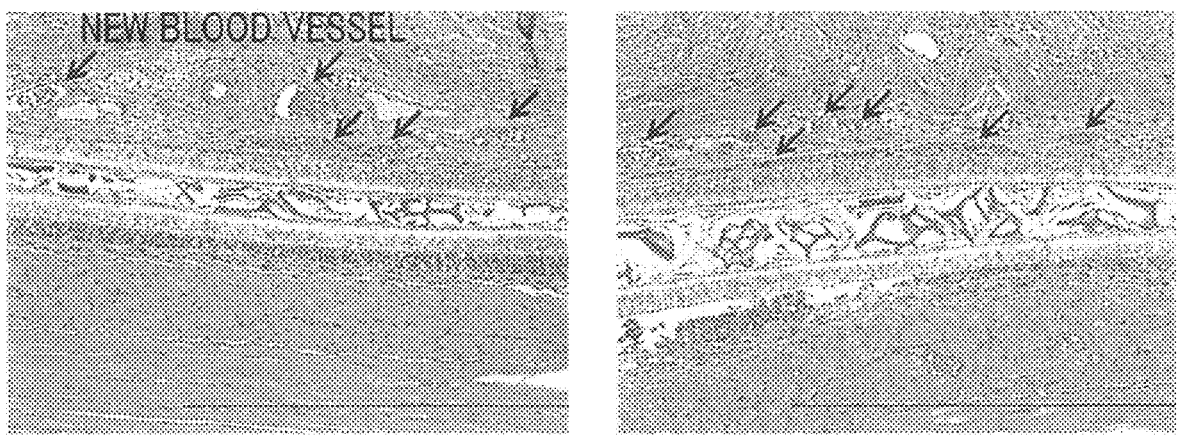
FIG. 11 illustrates a tissue specimen into which a cell transplant device including a cell structure is transplanted.

[Example 1] Evaluation of Ability to Induce Blood Vessels Around Device In Vivo 1,600 cell structures of mADSC produced in Reference Example 7 were sealed in the cell transplant devices (only an immunoisolation membrane) produced in Reference Examples 9, 11, and 13, and an injection part was sealed to complete the cell transplant devices (angiogenic agents). They were implanted subcutaneously in the back of a NOD/SCID mouse, and after 2 weeks, a tissue section of the transplantation site was produced to perform histological evaluation. A representative tissue specimen transplanted into two individuals is shown in FIG. 11. As a result, it was found that many new blood vessels were locally induced in the vicinity of the cell transplant device including the cell structure of a mesenchymal stem cell (MSC).

Figure 12:
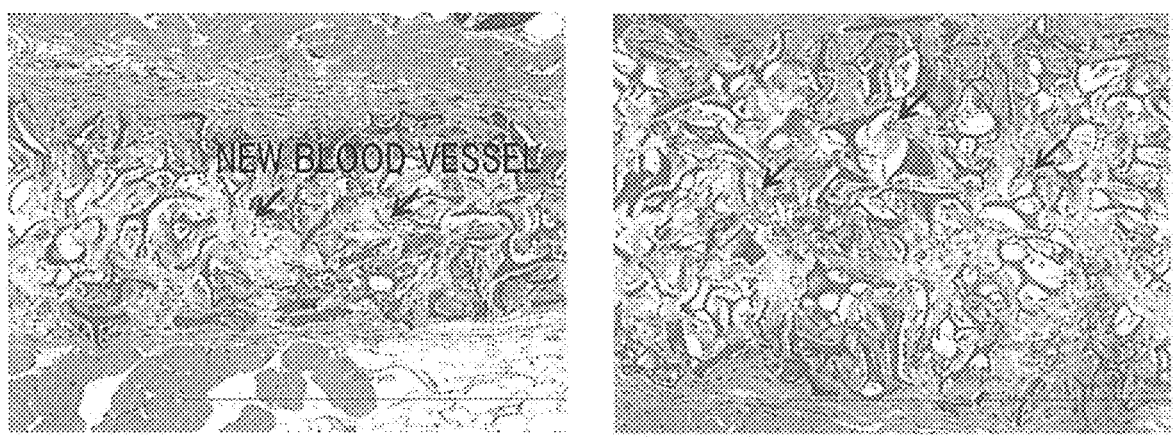
FIG. 12 illustrates a tissue specimen into which only a cell structure is transplanted.

[Comparative Example 1] Evaluation of Ability to Induce Blood Vessels Around Device In Vivo Only the cell structure of mADSC produced in Reference Example 7 was implanted subcutaneously on the back of a NOD/SCID mouse, and after 2 weeks, a tissue section of the transplantation site was produced to perform histological evaluation. A representative tissue specimen transplanted into two individuals is shown in FIG. 12. As a result, new blood vessels were induced at random sites in the case of only the cell structure of a mesenchymal stem cell (mADSC).

Figure 13:
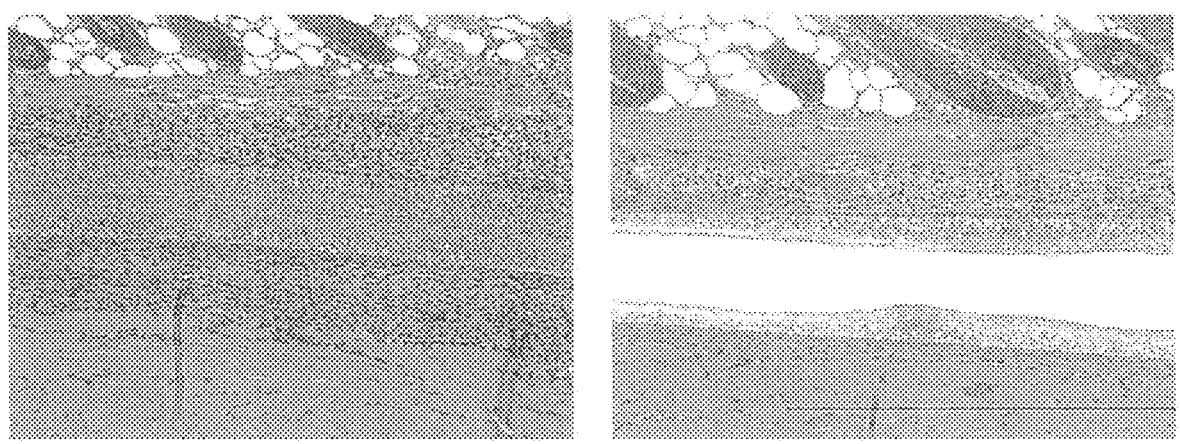
FIG. 13 illustrates a tissue specimen into which a cell transplant device (only an immunoisolation membrane) is transplanted.
Figure 14:
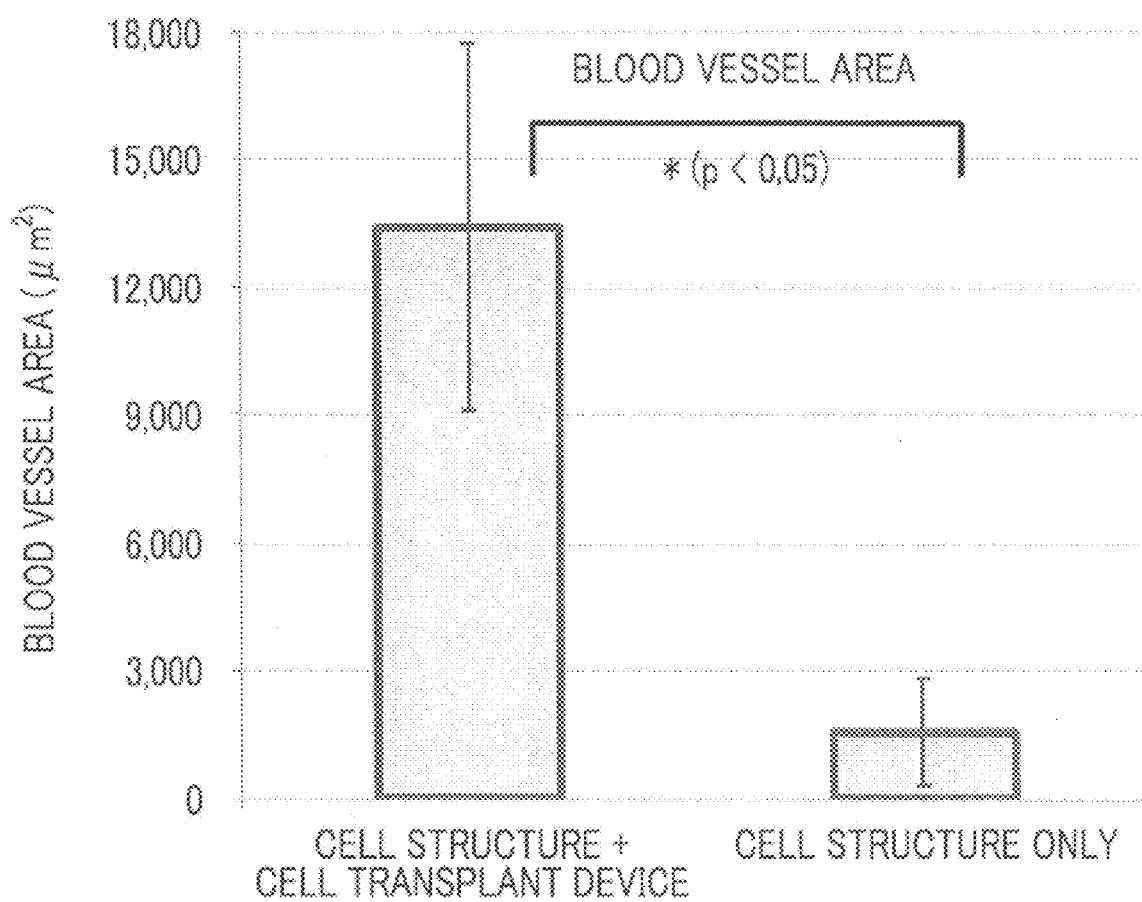
FIG. 14 illustrates measurement results of a total area of blood vessel per field of view.
Figure 15:
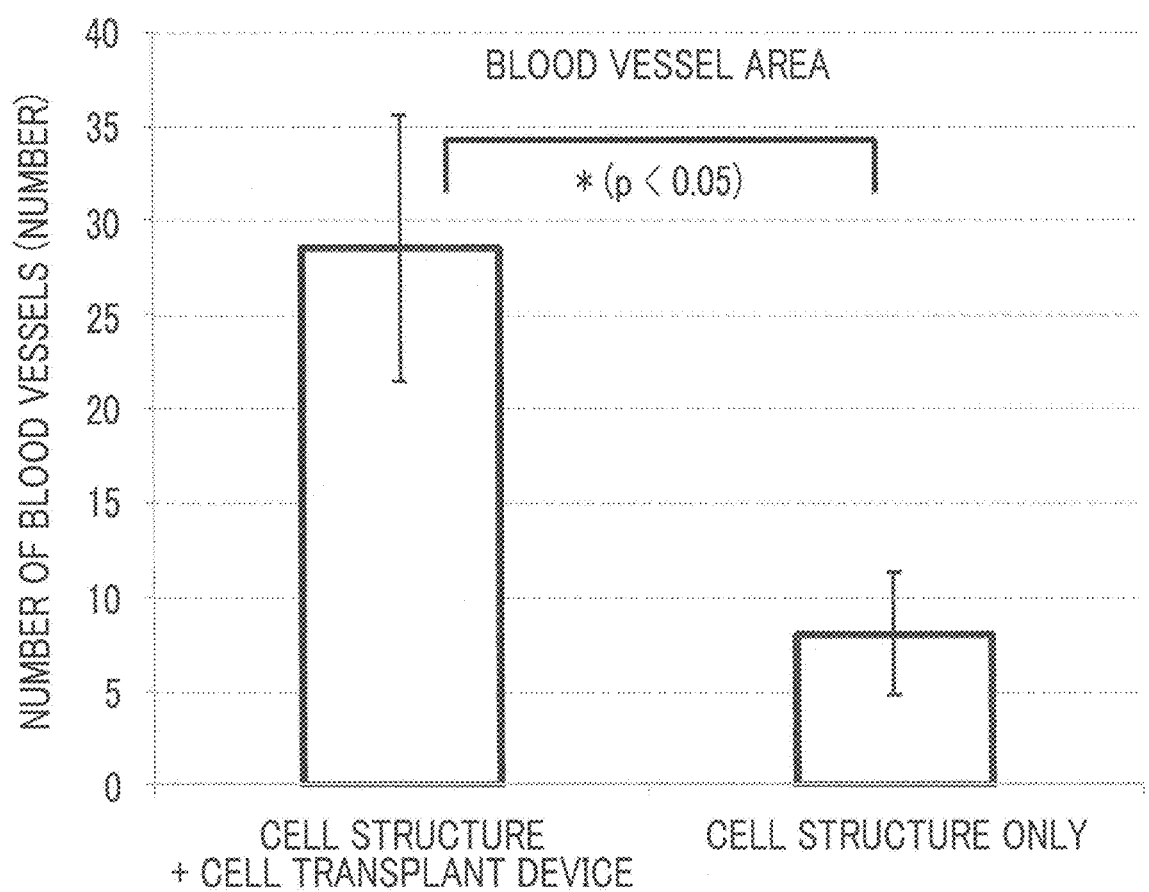
FIG. 15 illustrates measurement results of the number of blood vessels per field of view.
Figure 16:
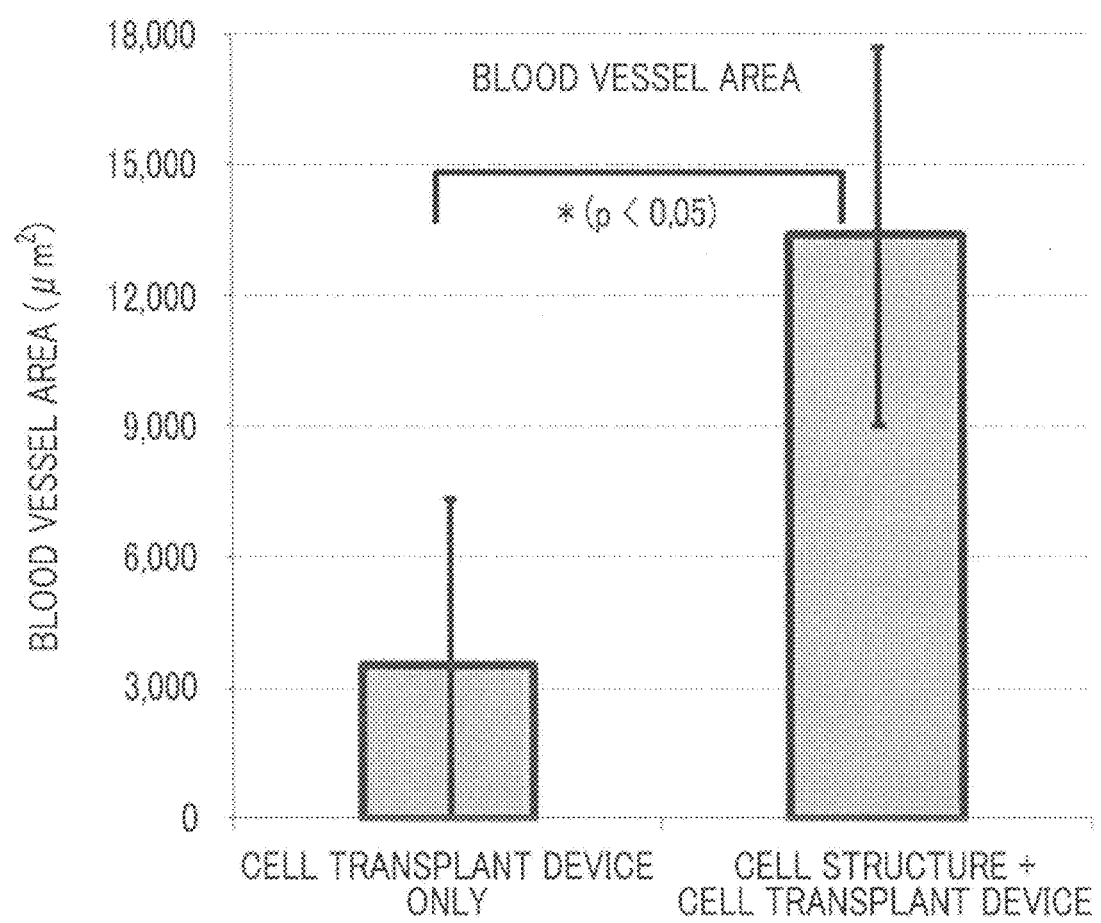
FIG. 16 illustrates measurement results of a total area of blood vessel per field of view.
Figure 17:
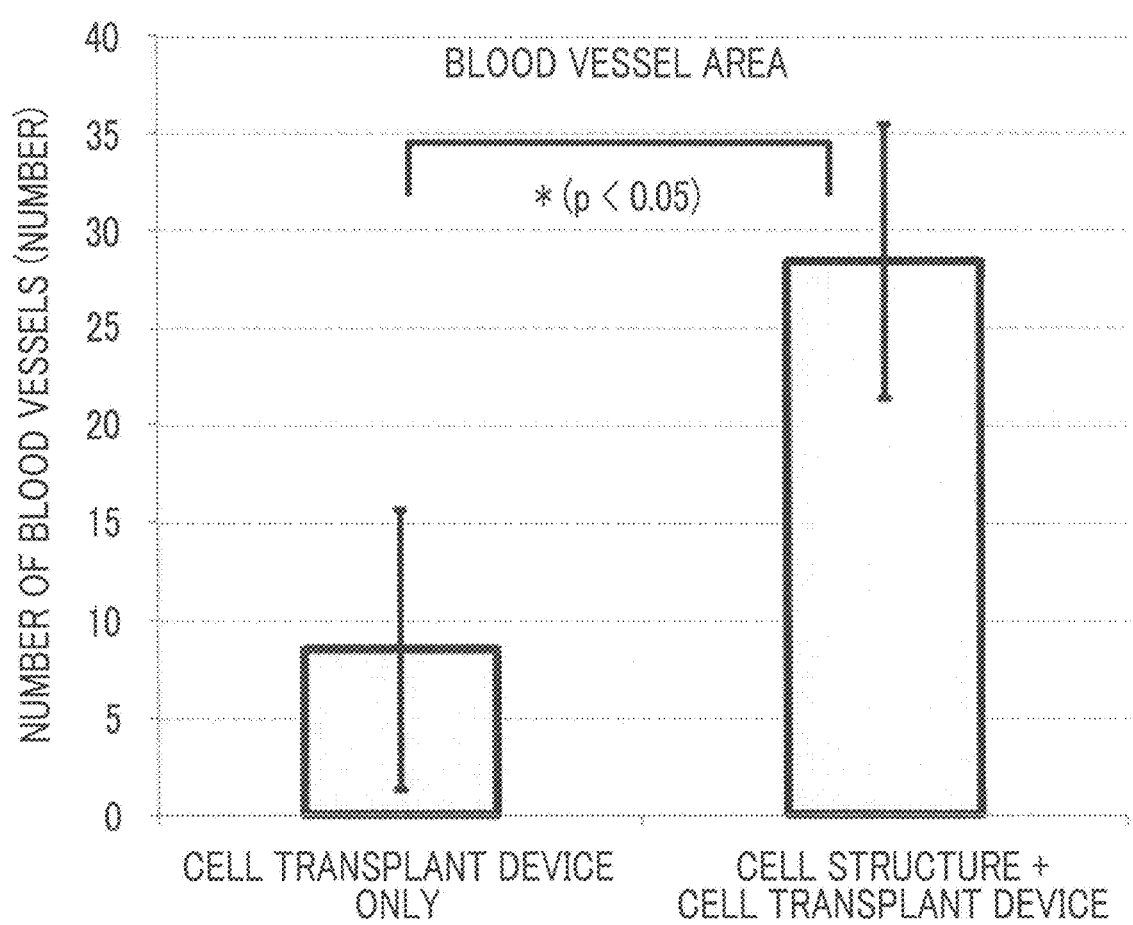
FIG. 17 illustrates measurement results of the number of blood vessels per field of view.

[Comparative Example 2] Evaluation of Ability to Induce Blood Vessels Around Device In Vivo The cell transplant devices produced in Reference Examples 9, 11, and 13 were implanted subcutaneously on the back of a NOD/SCID mouse, and after 2 weeks, tissue sections of the transplantation sites were produced to perform histological evaluation. A representative tissue specimen transplanted into two individuals is shown in FIG. 13. As a result, it was found that an amount of new blood vessels induced was very small in the cell transplant device not including the cell structure of a mesenchymal stem cell (mADSC).

Example 2

The results of Example 1 and Comparative Examples 1 and 2 were quantitatively evaluated based on a total area of blood vessels per visual field and the number of blood vessels per visual field. In the evaluation, data of 4 individuals were analyzed, and an average value and a standard deviation were calculated. As a result, in the transplantation results of the "cell structure+cell transplant device" (Example 1), in the vicinity of the device, a total area of blood vessel per visual field was 13,391±4,329 μm$^2$, and the number of blood vessels per visual field was 28.5±7.0. On the other hand, in the transplantation results of the "cell structure only" (Comparative Example 1), a total area of blood vessel per visual field was 1,571±1,264 μm$^2$, and the number of blood vessels per visual field was 8.0±3.2. According to the transplantation results of the "only the cell transplant device" (Comparative Example 2), a total area of blood vessel per visual field was 3,519±3,826 μm$^2$, and the number of blood vessels per visual field was 8.5±7.1. Based on these results, it became clear that, in the quantitative determination, the "cell structure+cell transplant device" induces a significantly large amount of new blood vessels around the device as compared to the "only the cell structure" or "only the cell transplant device" (refer to FIGS. 14 to 17). Regarding statistical analysis, by the t-test, it was found that there is a significant difference between the evaluation results of the total area of blood vessel and the evaluation results of the number of blood vessels between the "only the cell structure" or "only the cell transplant device" and the "cell structure+cell transplant device" ($p<0.05$).

[Example 3] Evaluation of Ability to Induce Blood Vessels Around Device In Vivo (Different Recipient Animals)

Figure 18:
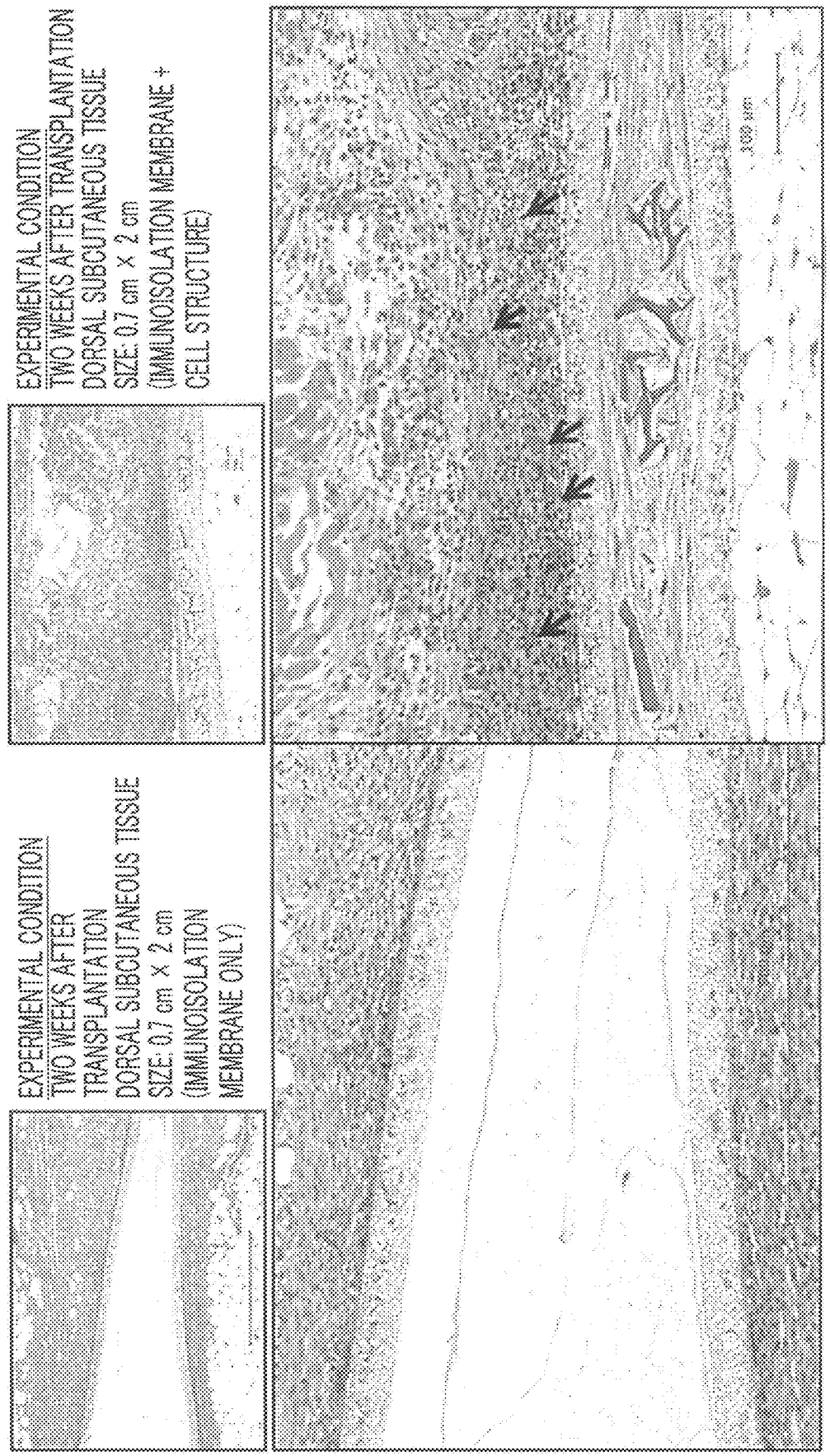
FIG. 18 illustrates a tissue specimen of a C57BL/6 mouse into which a cell transplant device including a cell structure, or a cell transplant device (only an immunoisolation membrane) is transplanted.

1,600 cell structures of mADSC produced in Reference Example 7 were sealed in the cell transplant device (only an immunoisolation membrane) produced in Reference Example 9, and an injection part was sealed to complete the cell transplant device. They were implanted subcutaneously in the back of a C57BL/6 mouse, and after 2 weeks, a tissue section of the transplantation site was produced to perform histological evaluation. In addition, a tissue specimen compared with the case where only the cell transplant device produced in Reference Example 9 was transplanted is shown in FIG. 18. As a result, it was found that, in the cell transplant device including the cell structure, even in a case of transplantation to the C57BL/6 mouse, a larger number of new blood vessels were induced in the vicinity of the device as compared to the case where the cell transplant device (an immunoisolation membrane only) was transplanted.

[Reference Example 14] Preparation of Spheroid $1.2 \times 10^8$ cells of mouse adipose-derived mesenchymal stem cells (mADSCs) suspended in 4 mL of a D-MEM medium (Dulbecco's modified Eagle medium) containing 10% FBS (fetal bovine serum) were seeded in EZSPHERE (registered trademark) dish Type 903 which is a cell non-adhesive dish of 35 mm (manufactured by AGC TECHNO GLASS CO., Ltd., a spheroid well diameter is 800 μm, a spheroid well depth is 300 μm, the number of spheroid wells is about 1,200, a bottom surface is a culture surface having recessed portions, and a side outer wall portion standing on the periphery of the culture surface is provided). The dish was allowed to stand for 48 hours at 37° C. in a $CO_2$ incubator to obtain about 1,200 uniform spheroids.

Figure 19:
FIG. 19 illustrates a tissue specimen of a C57BL/6 mouse into which only a cell transplant device is transplanted.

[Example 4] Evaluation of Ability to Induce Blood Vessels Around Device In Vivo 1,600 spheroids of mADSC produced in Reference Example 14 were sealed in the cell transplant device (only an immunoisolation membrane) produced in Reference Example 9, and an injection part was sealed to complete the cell transplant device (an angiogenic agent). They were implanted subcutaneously in the back of a C57BL/6 mouse, and after 2 weeks, a tissue section of the transplantation site was produced to perform histological evaluation. A representative tissue specimen transplanted into two individuals is shown in FIG. 19. As a result, it was found that new blood vessels were induced in the vicinity of the cell transplant device including mesenchymal stem cells (MSCs).

Example 5

Figure 20:
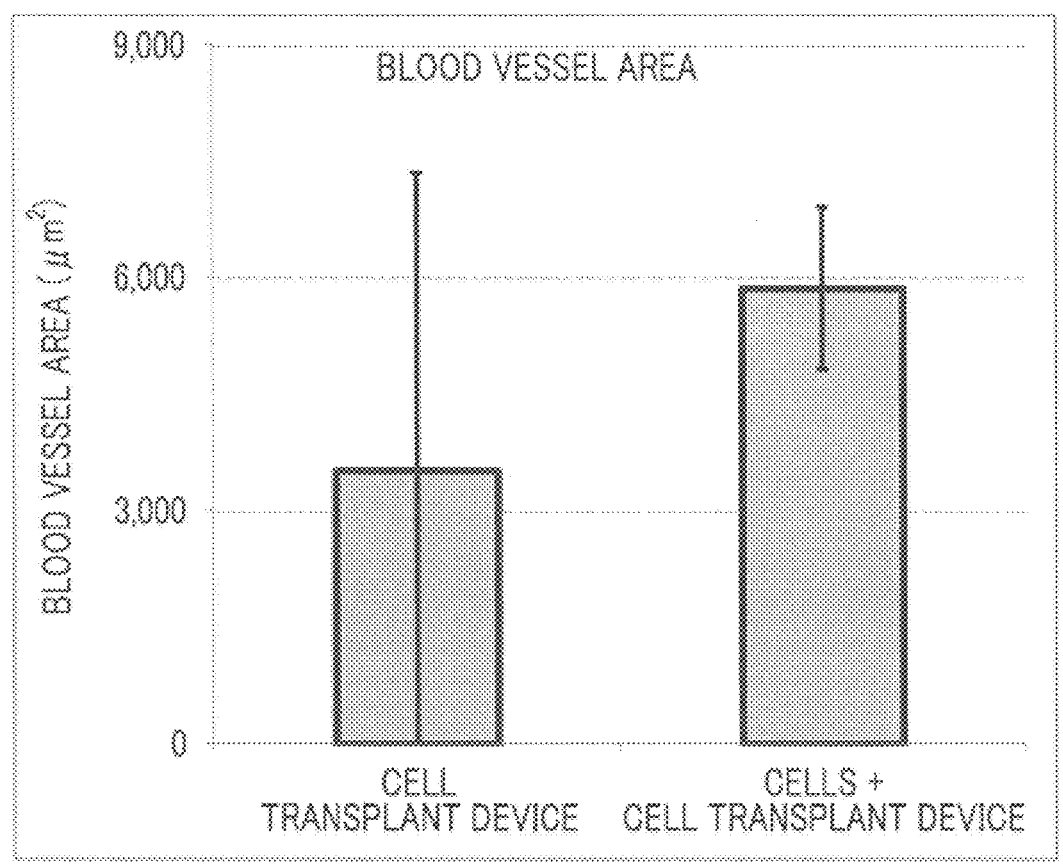
FIG. 20 illustrates measurement results of a total area of blood vessel per field of view.
Figure 21:
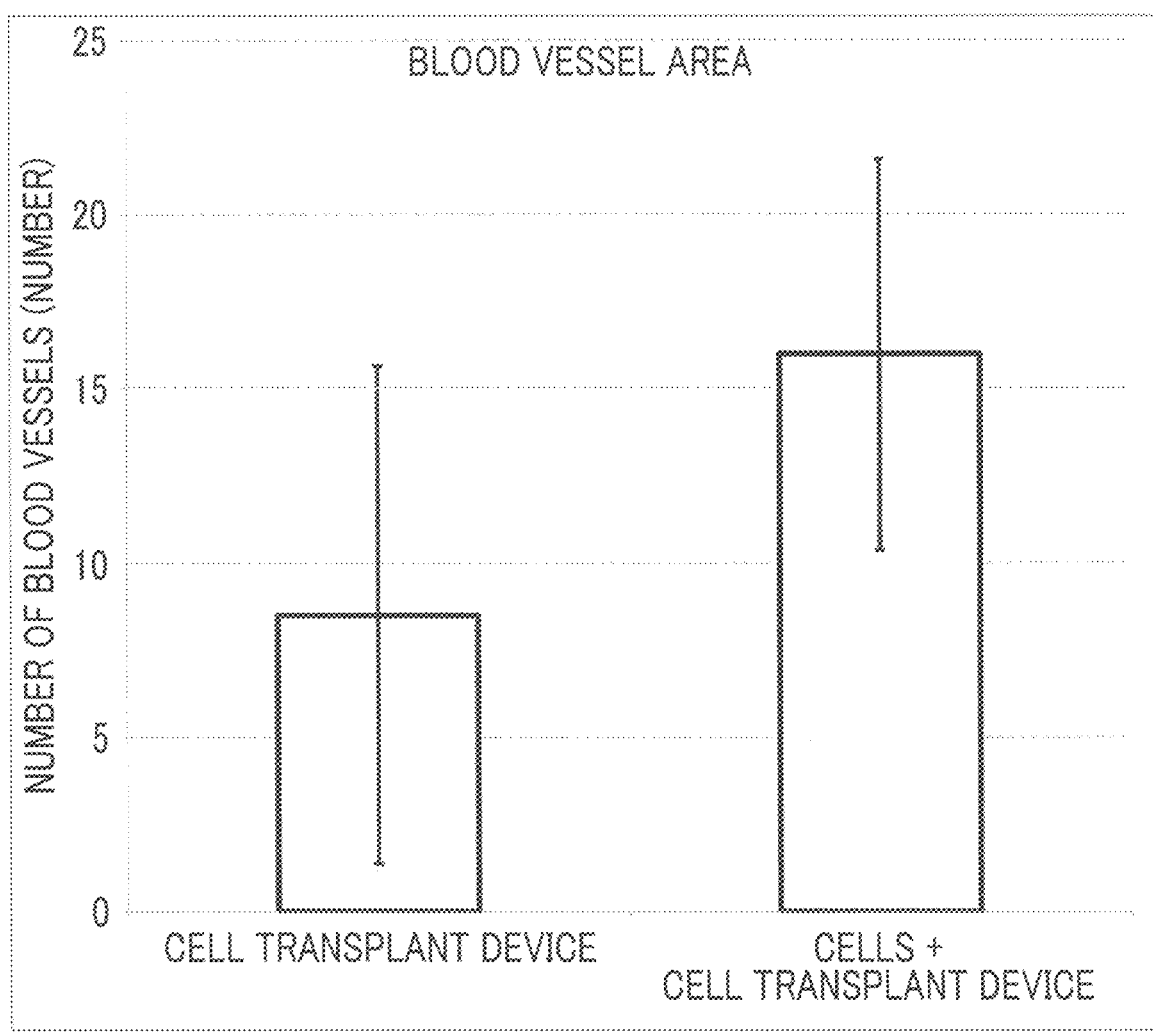
FIG. 21 illustrates measurement results of the number of blood vessels per field of view.

The results of Example 4 were quantitatively evaluated based on a total area of blood vessels per visual field and the number of blood vessels per visual field. In the evaluation, data of 4 individuals were analyzed, and an average value and a standard deviation were calculated. As a result, in the transplantation results of the "cells+cell transplant device" (Example 4), a total area of blood vessel per visual field was $5871 \pm 1053$ μm$^2$, and the number of blood vessels per visual field was $16 \pm 5.6$. Based on the results of Example 2 and Example 4, it became clear that the "cells+cell transplant device" induces a large amount of new blood vessels as compared to the "only the cell transplant device" (refer to FIGS. 20 and 21).

SEQUENCE LISTING

International Application 17F02810W1 Angiogenic Agent and Method for Manufacturing Same and JP1803216220180830-00210410351801780099 Normal 20180830145537201808061055230470_P1AP101_17_0. app Based on International Patent Cooperation Treaty

What is claimed is:

1. An angiogenesis method which comprises transplanting, to a subject in need of angiogenesis, a cell transplant device including a mesenchymal stem cell (A) and an immunoisolation membrane (B) that encloses the mesenchymal stem cell,
   wherein the immunoisolation membrane is a porous membrane comprising a thermoplastic or thermoset polymer and
   wherein within an inner side of the porous membrane, a layered compact portion in which a pore diameter is minimized is present, and the pore diameter continuously increases as a gradient in a thickness direction from the compact portion toward at least one surface of the porous membrane,
   wherein the porous membrane is a membrane formed from a single composition as a single layer.

2. The angiogenesis method according to claim 1, wherein the mesenchymal stem cell is an adipose-derived mesenchymal stem cell or a bone-marrow-derived mesenchymal stem cell.

3. The angiogenesis method according to claim 1, wherein the thermoplastic or thermoset polymer is selected from polysulfone or polyvinylpyrrolidone.

4. The angiogenesis method according to claim 3, wherein a minimum pore diameter of the porous membrane is 0.02 μm to 1.5 μm.

5. The angiogenesis method according to claim 3, wherein a thickness of the porous membrane is 10 μm to 250 μm.

6. The angiogenesis method according to claim 3, wherein a ratio of a maximum pore diameter to a minimum pore diameter of the porous membrane ranges from 3:1 to 20:1.

7. The angiogenesis method according to claim 1, wherein a thickness of the compact portion is 0.5 μm to 30 μm.

8. The angiogenesis method according to claim 1, wherein the mesenchymal stem cell is contained as a cell structure which includes a plurality of biocompatible polymer blocks and a plurality of mesenchymal stem cells of at least one type, and in which at least one of the biocompatible polymer blocks is disposed in gaps between the plurality of mesenchymal stem cells.

9. The angiogenesis method according to claim 8, wherein a size of one of the biocompatible polymer blocks is 20 μm to 200 μm.

10. The angiogenesis method according to claim 8, wherein, in the biocompatible polymer blocks, a biocompatible polymer is cross-linked by heat, ultraviolet rays, or an enzyme.

11. The angiogenesis method according to claim 8, wherein the biocompatible polymer blocks have an amorphous shape.

12. The angiogenesis method according to claim 8, wherein the cell structure includes 0.0000001 μg to 1 μg of the biocompatible polymer blocks per cell.

* * * * *

```
                        SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160
```

```
Leu Pro Gly Pro Lys Gly Glu Arg Gly Asp Ala Gly Pro Lys Gly Ala
            165                 170                 175

Asp Gly Ala Pro Gly Lys Asp Gly Val Arg Gly Leu Ala Gly Pro Pro
        180                 185                 190

Gly Ala Pro Gly Leu Gln Gly Ala Pro Gly Leu Gln Gly Met Pro Gly
    195                 200                 205

Glu Arg Gly Ala Ala Gly Leu Pro Gly Pro Lys Gly Glu Arg Gly Asp
210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
            245                 250                 255

Glu Arg Gly Asp Ala Gly Pro Lys Gly Ala Asp Gly Ala Pro Gly Lys
        260                 265                 270

Asp Gly Val Arg Gly Leu Ala Gly Pro Ile Gly Pro Pro Gly Glu Arg
    275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
        340                 345                 350

Pro Lys Gly Glu Arg Gly Asp Ala Gly Pro Lys Gly Ala Asp Gly Ala
    355                 360                 365

Pro Gly Lys Asp Gly Val Arg Gly Leu Ala Gly Pro Pro Gly Ala Pro
370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
            405                 410                 415

Lys Gly Ala Asp Gly Ala Pro Gly Ala Pro Gly Leu Gln Gly Met Pro
        420                 425                 430

Gly Glu Arg Gly Ala Ala Gly Leu Pro Gly Pro Lys Gly Glu Arg Gly
    435                 440                 445

Asp Ala Gly Pro Lys Gly Ala Asp Gly Ala Pro Gly Lys Asp Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
            485                 490                 495

Ala Asp Gly Ala Pro Gly Lys Asp Gly Val Arg Gly Leu Ala Gly Pro
        500                 505                 510

Ile Gly Pro Pro Gly Pro Ala Gly Ala Pro Gly Ala Pro Gly Leu Gln
    515                 520                 525

Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 7
```

-continued

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(571)
<223> OTHER INFORMATION: Every Xaa can be any naturally occurring amino
      acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95

```
Gly Xaa Xaa Gly Xaa Xaa Gly Xaa Xaa Gly Xaa Xaa Gly
        100             105             110
Xaa Xaa Gly Xaa Xaa Gly Xaa Xaa Gly Xaa Xaa Gly Xaa
        115             120             125
Xaa Gly Xaa Xaa Gly Xaa Xaa Gly Xaa Xaa Gly Xaa Xaa
        130             135             140
Gly Xaa Xaa Gly Xaa Xaa Gly Xaa Xaa Gly Xaa Xaa Gly
145             150             155             160
Xaa Xaa Gly Xaa Xaa Gly Xaa Xaa Gly Xaa Xaa Gly Xaa
        165             170             175
Xaa Gly Xaa Xaa Gly Xaa Xaa Gly Xaa Xaa Gly Xaa Xaa
        180             185             190
Gly Xaa Xaa Gly Xaa Xaa Gly Xaa Xaa Gly Xaa Xaa Gly
        195             200             205
Xaa Xaa Gly Xaa Xaa Gly Xaa Xaa Gly Xaa Xaa Gly Xaa
        210             215             220
Xaa Gly Xaa Xaa Gly Xaa Xaa Gly Xaa Xaa Gly Xaa Xaa
225             230             235             240
Gly Xaa Xaa Gly Xaa Xaa Gly Xaa Xaa Gly Xaa Xaa Gly
        245             250             255
Xaa Xaa Gly Xaa Xaa Gly Xaa Xaa Gly Xaa Xaa Gly Xaa
        260             265             270
Xaa Gly Xaa Xaa Gly Xaa Xaa Gly Xaa Xaa Gly Xaa Xaa
        275             280             285
Gly Xaa Xaa Gly Xaa Xaa Gly Xaa Xaa Gly Xaa Xaa Gly
        290             295             300
Xaa Xaa Gly Xaa Xaa Gly Xaa Xaa Gly Xaa Xaa Gly Xaa
305             310             315             320
Xaa Gly Xaa Xaa Gly Xaa Xaa Gly Xaa Xaa Gly Xaa Xaa
        325             330             335
Gly Xaa Xaa Gly Xaa Xaa Gly Xaa Xaa Gly Xaa Xaa Gly
        340             345             350
Xaa Xaa Gly Xaa Xaa Gly Xaa Xaa Gly Xaa Xaa Gly Xaa
        355             360             365
Xaa Gly Xaa Xaa Gly Xaa Xaa Gly Xaa Xaa Gly Xaa Xaa
        370             375             380
Gly Xaa Xaa Gly Xaa Xaa Gly Xaa Xaa Gly Xaa Xaa Gly
385             390             395             400
Xaa Xaa Gly Xaa Xaa Gly Xaa Xaa Gly Xaa Xaa Gly Xaa
        405             410             415
Xaa Gly Xaa Xaa Gly Xaa Xaa Gly Xaa Xaa Gly Xaa Xaa
        420             425             430
Gly Xaa Xaa Gly Xaa Xaa Gly Xaa Xaa Gly Xaa Xaa Gly
        435             440             445
Xaa Xaa Gly Xaa Xaa Gly Xaa Xaa Gly Xaa Xaa Gly Xaa
        450             455             460
Xaa Gly Xaa Xaa Gly Xaa Xaa Gly Xaa Xaa Gly Xaa Xaa
465             470             475             480
Gly Xaa Xaa Gly Xaa Xaa Gly Xaa Xaa Gly Xaa Xaa Gly
        485             490             495
Xaa Xaa Gly Xaa Xaa Gly Xaa Xaa Gly Xaa Xaa Gly Xaa
        500             505             510
Xaa Gly Xaa Xaa Gly Xaa Xaa Gly Xaa Xaa Gly Xaa Xaa
```

-continued

```
            515                 520                 525
Gly Xaa Xaa Gly Xaa Xaa Gly Xaa Xaa Gly Xaa Xaa Gly Xaa Xaa Gly
        530                 535                 540
Xaa Xaa Gly Xaa Xaa Gly Xaa Xaa Gly Xaa Xaa Gly Xaa Xaa Gly Xaa
545                 550                 555                 560
Xaa Gly Xaa Xaa Gly Xaa Xaa Gly Xaa Xaa Gly
                565                 570
```